United States Patent [19]

Levitt

[11] 4,127,405

[45] Nov. 28, 1978

[54] HERBICIDAL SULFONAMIDES

[75] Inventor: George Levitt, Wilmington, Del.

[73] Assignee: E. I. Du Pont de Nemours and Company, Wilmington, Del.

[21] Appl. No.: 824,805

[22] Filed: Aug. 15, 1977

Related U.S. Application Data

[63] Continuation-in-part of Ser. No. 769,914, Feb. 23, 1977, abandoned, which is a continuation-in-part of Ser. No. 674,668, Apr. 7, 1976, abandoned.

[51] Int. Cl.² .................. C07D 251/44; C07D 251/46; A01N 9/16

[52] U.S. Cl. ........................................ 71/93; 544/211; 544/212

[58] Field of Search ...................... 544/211, 212; 71/93

[56] References Cited

FOREIGN PATENT DOCUMENTS 121,788  9/1966  Netherlands.

*Primary Examiner*—John M. Ford

[57] ABSTRACT

N-(1,3,5-triazin-2-ylaminocarbonyl) arylsulfonamides, such as N-[(4,6-dimethyl-1,3,5-triazin-2-yl)aminocarbonyl]benzenesulfonamide, are useful for the regulation of plant growth and as herbicides, particularly for controlling nutsedge.

114 Claims, No Drawings

HERBICIDAL SULFONAMIDES

CROSS-REFERENCE TO RELATED APPLICATIONS

This application is a continuation-in-part of my U.S. application Ser. No. 769,914, filed Feb. 23, 1977, now abandoned, which is a continuation-in-part of my U.S. application Ser. No. 674,668, filed Apr. 7, 1976, now abandoned.

BACKGROUND

This invention relates to novel N-[(1,3,5-triazin-2-yl)aminocarbonyl]arylsulfonamides useful as agricultural chemicals.

Netherlands Patent No. 121,788, published Sept. 15, 1966, teaches the preparation of compounds of Formula (i), and their use as general or selective herbicides,

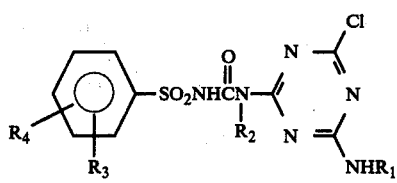

(i)

wherein
$R_1$ and $R_2$ may independently be alkyl of 1–4 carbon atoms; and
$R_3$ and $R_4$ may independently be hydrogen, chlorine or alkyl of 1–4 carbon atoms.

Compounds of Formula (ii), and their use as antidiabetic agents, are reported in *J. Drug Res.* 6, 123 (1974)

(ii)

wherein R is pyridyl.

The presence of undesired vegetation causes substantial damage to useful crops, especially agricultural products that satisfy man's basic food needs, such as soybeans, corn, wheat, and the like. The current population explosion and concomitant world food shortage demand improvements in the efficiency of producing these crops. Preventing or minimizing the loss of a portion of such valuable crops by killing, or inhibiting the growth of undesired vegetation is one way of improving this efficiency.

A wide variety of materials useful for killing, or inhibiting (controlling) the growth of undesired vegetation is available; such materials are commonly referred to as herbicides. However, the need exists for still more effective herbicides that destroy or retard weeds without causing significant damage to useful crops. Some weeds (nutsedge is a particular example) are very difficult to control; many of the herbicides that are used to control nutsedge are so nonselective that they cause damage to the crops themselves.

SUMMARY OF THE INVENTION

According to this invention, there is provided compounds of Formula I and their agriculturally suitable salts, suitable agricultural compositions containing them, and methods of using them as selective, as well as general herbicides having both preemergence and postemergence activity. These compounds are highly active herbicides. They are especially useful for controlling weeds in wheat.

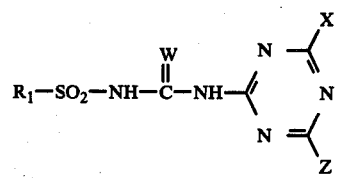

I.

wherein
$R_1$ is

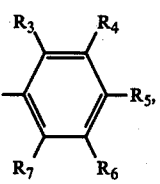, 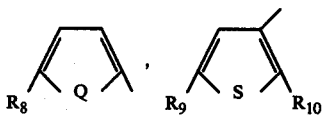,

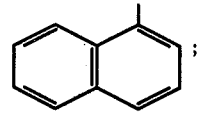;

$R_3$ and $R_6$ are independently hydrogen, fluorine, chlorine, bromine, iodine, alkyl of 1–4 carbon atoms, alkoxy of 1–4 carbon atoms, nitro, trifluoromethyl, cyano, $CH_3S(O)_n—$ or $CH_3CH_2S(O)_n—$;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1–2 carbon atoms or alkoxy of 1–2 carbon atoms;

$R_8$ is hydrogen, methyl, chlorine or bromine;

$R_9$ and $R_{10}$ are independently hydrogen, methyl, chlorine or bromine;

W and Q are independently oxygen or sulfur;

$n$ is 0, 1 or 2;

X is hydrogen, chlorine, bromine, methyl, ethyl, alkoxy of 1–3 carbon atoms, trifluoromethyl, $CH_3S—$ or $CH_3OCH_2—$; and Z is methyl or methoxy; or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

Preferred in order of increasing preference based on activity or cost or both are:

(1) those compounds of Formula I, defined above, wherein $R_1$ is

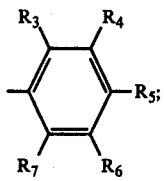

(2) compounds of preference (1) wherein
  $R_3$ is hydrogen, fluorine, chlorine, bromine, alkyl of 1-4 carbon atoms, alkoxy of 1-4 carbon atoms, nitro, $CH_3S-$ or $CH_3CH_2S-$; and
  $R_5$ is hydrogen, fluorine, chlorine, bromine or methyl; and
  $R_6$ is hydrogen, fluorine, chlorine, bromine, alkyl of 1-4 carbon atoms, alkoxy of 1-4 carbon atoms, trifluoromethyl, nitro, $CH_3S-$ or $CH_3CH_2S-$;
  provided that:
  (a) when $R_5$ is other than hydrogen, $R_3$, $R_6$ or $R_7$ must independently be hydrogen, fluorine, chlorine, bromine, methyl or methoxy, and $R_4$ must be hydrogen, fluorine, chlorine, bromine or methyl;
(3) compounds of preference (2) wherein X is methyl or alkoxy of 1-3 carbon atoms; and Z is methoxy;
(4) compounds of preference (3) wherein
  $R_3$ is hydrogen, fluorine, chlorine, bromine, alkyl of 1-2 carbon atoms, alkoxy of 1-2 carbon atoms, nitro, $CH_3S-$ or $CH_3CH_2S-$; and
  $R_4$, $R_5$ and $R_7$ are independently hydrogen, fluorine, chlorine or methyl; and
  $R_6$ is hydrogen, fluorine, chlorine, bromine, alkyl of 1-2 carbon atoms, alkoxy of 1-2 carbon atoms, trifluoromethyl, nitro, $CH_3S-$, or $CH_3CH_2S-$;
(5) compounds of preference (3) wherein
  $R_3$, $R_4$, $R_5$, $R_6$ and $R_7$ are independently hydrogen, fluorine, chlorine or methyl;
(6) compounds of preference (3) wherein
  $R_3$ is fluorine, chlorine or methyl; and
  $R_4$, $R_5$, $R_6$ and $R_7$ are independently hydrogen, fluorine, chlorine or methyl;
  provided that:
  when $R_5$ is other than hydrogen, $R_4$ and $R_6$ must be hydrogen;
(7) compounds of preference (3) wherein
  $R_3$ is fluorine, chlorine or methyl; and
  $R_4$ and $R_6$ are hydrogen; and
  $R_5$ and $R_7$ are independently hydrogen, fluorine, chlorine or methyl;
(8) compounds of preference (3) wherein
  $R_3$ is hydrogen, fluorine, chlorine, bromine, alkyl of 1-4 carbon atoms, alkoxy of 1-4 carbon atoms, $CH_3S-$, or $CH_3CH_2S-$; and
  $R_4$ $R_5$ and $R_7$ are hydrogen; and
  $R_6$ is hydrogen, fluorine, chlorine, bromine, alkyl of 1-4 carbon atoms, alkoxy of 1-4 carbon atoms, trifluoromethyl, nitro, $CH_3S-$ or $CH_3CH_2S$;
(9) compounds of preference (8) wherein
  $R_3$ is fluorine, chlorine, bromine, alkyl of 1-2 carbon atoms or alkoxy of 1-2 carbon atoms; and
  $R_6$ is hydrogen, fluorine, chlorine, bromine, alkyl of 1-2 carbon atoms, alkoxy of 1-2 carbon atoms, trifluoromethyl or nitro; and
(10) compounds of preference (8) wherein
  $R_3$ is fluorine, chlorine, bromine, methyl or methoxy;
  $R_6$ is hydrogen, fluorine, chlorine, bromine, methyl, methoxy or nitro; and
(11) compounds of preference (4) wherein $R_3$ is nitro and each of $R_4$, $R_5$, $R_6$ and $R_7$ is hydrogen.

Also, preferred in order of increasing preference based on activity or cost or both are:
(A) those compounds of Formula I, defined above, wherein

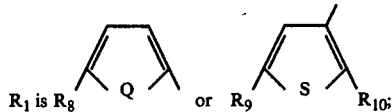

(B) compounds of preference (A) wherein
  Q is sulfur;
  X is methyl or alkoxy of 1-3 carbon atoms; and
  Z is methoxy;
(C) Compounds of preference (A) wherein
  $R_1$ is

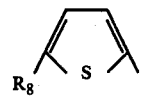

and $R_8$ is hydrogen.

Similarly, preferred based on activity are those compounds of Formula I, defined above, wherein
(1) $R_1$ is

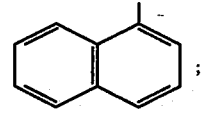

and W is oxygen.

Specifically, preferred for their outstanding activity or highly favorable cost or both are:

(1) N-[(4-methoxy-6-methyl-1,3,5-triazin-2-yl)aminocarbonyl]-2-chlorobenzenesulfonamide, m.p. 174°-178° C.;
(2) N-[(4,6-dimethoxy-1,3,5-triazin-2-yl)aminocarbonyl]-2-chlorobenzenesulfonamide, m.p. 188°-189° C.;
(3) N-[(4,6-dimethoxy-1,3,5-triazin-2-yl)aminocarbonyl]-2,5-dimethoxybenzenesulfonamide, m.p. 187°-188° C.;
(4) N-[(4-methoxy-6-methyl-1,3,5-triazin-2-yl)aminocarbonyl]-2-nitrobenzenesulfonamide, m.p. 178°-181° C.;
(5) N-[(4,6-dimethoxy-1,3,5-triazin-2-yl)aminocarbonyl]-2-nitrobenzenesulfonamide, m.p. 175°-178° C.; and
(6) N-[(4-methoxy-6-methyl-1,3,5-triazin-2-yl) aminocarbonyl]-2,6-dichlorobenzenesulfonamide, m.p. 203°-206° C.

In addition to having excellent activity for broad spectrum control of vegetation, the compounds of Formula I are also useful for selective control of weeds in wheat, brush control and water hyacinth control. Moreover, the compounds of Formula I are useful plant growth regulants, e.g. increasing sugar content in sugarcane and sorghum and suppressing seed head formation in grasses such as Bahia grass.

Specifically, preferred (A) for their selective control of weeds in wheat are:
  (1) N-[(4-methoxy-6-methyl-1,3,5-triazin-2-yl)aminocarbonyl]-2-chlorobenzenesulfonamide, m.p. 174°–178° C.;
  (2) N-[(4,6-dimethoxy-1,3,5-triazin-2-yl)aminocarbonyl]-2-chlorobenzenesulfonamide, m.p. 188°–189° C.; and
  (3) N-[(4,6-dimethoxy-1,3,5-triazin-2-yl)aminocarbonyl]-2,5-dimethoxybenzenesulfonamide, m.p. 187°–188° C.

(B) for selective control of brush is:
  (1) N-[(4,6-dimethoxy-1,3,5-triazin-2-yl)aminocarbonyl]benzenesulfonamide, m.p. 183°–185° C.;

(C) for their control of water hyacinth are:
  (1) N-[(4-methoxy-6-methyl-1,3,5-triazin-2-yl)aminocarbonyl]-2-chlorobenzenesulfonamide, m.p. 174°–178° C.;
  (2) N-[(4,6-dimethoxy-1,3,5-triazin-2-yl)aminocarbonyl]benzenesulfonamide, m.p. 183°–185° C.; and
  (3) N-[(4-methoxy-6-methyl-1,3,5-triazin-2-yl)aminocarbonyl]-2-chloro-5-methoxybenzenesulfonamide, m.p. 175°–176° C.;

(D) for growth regulant use are:
  (1) N-[(4,6-dimethoxy-1,3,5-triazin-2-yl)aminocarbonyl]benzenesulfonamide, m.p. 183°–185° C.;
  (2) N-[(4-methoxy-6-methyl-1,3,5-triazin-2-yl)aminocarbonyl]benzenesulfonamide;
  (3) N-[(4,6-dimethyl-1,3,5-triazin-2-yl)aminocarbonyl]benzenesulfonamide, m.p. 200°–201° C.; and
  (4) N-[(4-methoxy-6-methyl-1,3,5-triazin-2-yl)aminocarbonyl]-2-chlorobenzenesulfonamide, m.p. 174°–178° C.

Synthesis

As shown in Equation 1, the compounds of Formula I can be prepared by combining an appropriate 2-amino-1,3,5-triazine of Formula III with an appropriately substituted sulfonyl isocyanate or isothiocyanate of Formula II; $R_1$, $W$, $X$ and $Z$ being as previously defined.

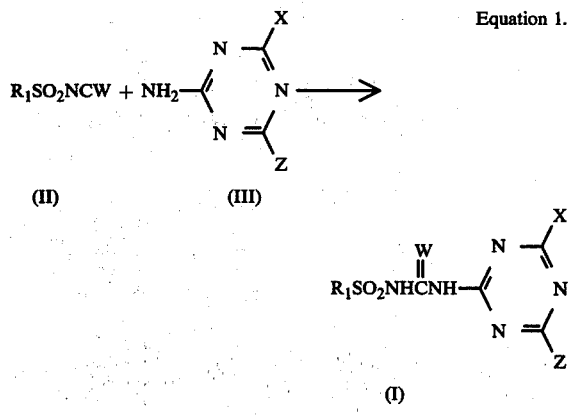

Equation 1.

The reaction is best carried out in inert aprotic organic solvents such as methylene chloride, tetrahydrofuran or acetonitrile, at ambient pressure and temperature. The mode of addition is not critical; however, it is often convenient to add the sulfonyl isocyanate or isothiocyanate to a stirred suspension of the aminotriazine. Since such isocyanates and isothiocyanates usually are liquids, their addition is more easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane, ethyl ether, or pentane, and filtration.

In certain cases, it may be possible to obtain isomeric products from the reaction shown in Equation 1. Such isomeric products would result from addition of compound II to an endocyclic nitrogen atom of aminotriazine III and have the structure exemplified below:

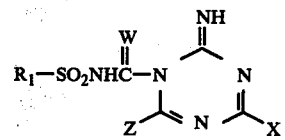

It is to be understood that the products resulting from the addition of a compound of Formula II to the exocyclic as well as the endocyclic nitrogen atoms of triazine III are to be considered a part of this invention.

The intermediate sulfonyl isocyanates of Formula II (wherein W is O) can be prepared by reacting corresponding sulfonamides with phosgene in the presence of n-butyl isocyanate are reflux in a solvent such as chlorobenzene, according to the procedure of H. Ulrich and A. A. Y. Sayigh, *Newer Methods of Preparative Organic Chemistry*, Vol. VI p 223–241, Academic Press, New York and London, W. Foerst Ed. In cases where formation of the desired sulfonyl isocyanate is difficult by the above procedure the sulfonyl urea formed by reaction of butyl isocyanate with the appropriate sulfonamide is treated with phosgene according to the above reference.

The preparation of sulfonamides from ammonium hydroxide and sulfonyl chlorides is widely reported in the literature, e.g. Crossley et al., *J. Am. Chem. Soc.* 60, 2223 (1938). See also *J. Org. Chem.* 18, 894 (1953) for the preparation of 2-furansulfonamide.

Certain sulfonyl chlorides are best prepared by chlorosulfonation of a substituted benzene, naphthalene, or thiophene according to the teaching of H. T. Clarke et al. *Org. Synth.* Coll. Vol. 1, 2nd Ed. 1941, p. 85. Other benzenesulfonyl chlorides are best made by diazotization of the appropriate aniline with sodium nitrate in HCl, followed by reaction of the diazonium salt with sulfur dioxide and cuprous chloride in acetic acid according to the teaching of H. L. Yale and F. Sowinski, *J. Org. Chem.* 25 1824 (1960).

Furansulfonyl chlorides are best prepared as shown in Equation 2.

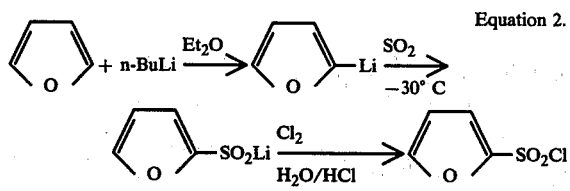

Equation 2.

Sulfonyl isothiocyanates can be prepared by treatment of sulfonamides with carbon disulfide and potassium hydroxide followed by reaction of the dipotassium salt with phosgene according to the teaching of K. Hartke, *Arch. Pharm.*, 299, 174 (1966).

2-Amino-1,3,5-triazines can be synthesized according to methods described by E. M. Smolin and L. Rapoport, supra, and by K. R. Huffman and F. C. Shaefer, U.S. Pat. No. 3,154,547.

Agriculturally suitable salts of compounds of Formula I are also useful herbicides and can be prepared by a number of ways known to the art. For example, metal salts can be made by treating compounds of Formula I with a solution of an alkali or alkaline earth metal salt having a sufficiently basic anion (e.g. hydroxide, alkoxide, carbonate or hydride). Quaternary amine salts can be made by similar techniques.

Salts of compounds of Formula I can also be prepared by exchange of one cation for another. Cationic exchange can be effected by direct treatment of an aqueous solution of a salt of a compound of Formula I (e.g., alkali metal or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g. an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble.

Acid addition salts, useful in this invention, can be obtained by reacting a compound of Formula I with a suitable acid, e.g. p-toluenesulfonic acid, trichloroacetic acid or the like.

The compounds of this invention and their preparation are further illustrated by the following examples wherein temperatures are given in degrees centigrade.

EXAMPLE 1

N-[(4,6-Dimethyl-1,3,5-triazin-2-yl)aminocarbonyl]-2-methylbenzenesulfonamide

To 12.3 g 2-amino-4,6-dimethyl-1,3,5-triazine in 250 ml of dry acetonitrile was added, with stirring, 19.7 g of 2-methylbenzenesulfonyl isocyanate at a rate designed to avoid excessive heating of the reaction mixture. Stirring was continued until the desired product crystallized. The product was removed by filtration, washed with a small amount of ethyl ether and dried. The resulting product, N-[(4,6-dimethyl-1,3,5-triazin-2-yl)aminocarbonyl]-2-methylbenzenesulfonamide, melted at 141°–145° C.

EXAMPLE 2

N-[(4,6-Dimethyl-1,3,5-triazin-2-yl)aminocarbonyl]-2-chlorobenzenesulfonamide

To 12.3 g of 2-amino-4,6-dimethyl-1,3,5-triazine in 200 ml of acetonitrile was added with stirring 21.7 g of 2-chlorobenzenesulfonyl isocyanate. All of the solid dissolved after the reagents were added and the mixture was then evaporated to dryness. The solid residue was triturated with ethyl ether and isolated by filtration to give impure N-[(4,6-dimethyl-1,3,5-triazin-2-yl)aminocarbonyl]-2-chlorobenzenesulfonamide melting at 115°–118° C. The nuclear magnetic resonance absorption spectrum of this product, in trifluoroacetic acid, showed singlet peaks at 2.69 and 2.9 parts per million.

EXAMPLE 3

N-[(4,6-dimethoxy-1,3,5-triazin-2-yl)aminocarbonyl]-2-chlorobenzenesulfonamide

To 15.6 g of 2-amino-4,6-dimethoxy-1,3,5-triazine in 300 ml of dry methylene chloride containing 0.1 g 1,4-diazabicyclo[2,2,2]octane was added 21 g 2-chlorobenzenesulfonyl isocyanate with stirring. The mixture was stirred for 16 hours and the resultant solid was removed by filtration. After washing the solid with 1-chlorobutane, the resulting product, N-[(4,6-dimethoxy-1,3,5-triazin-2-yl)-aminocarbonyl]-2-chlorobenzenesulfonamide melted at 188°–189° C. Infrared absorption analysis showed absorption peaks at 1740 cm$^{-1}$, 1630 cm$^{-1}$ and 1595 cm$^{-1}$ which are typical for this type of compound.

By using the procedure of Examples 1–3 with an equivalent amount of the appropriate aminotriazine and the appropriately substituted sulfonyl isocyanate, the compounds given in Table I can be prepared:

Table I-A

| X | Z | m.p. |
|---|---|---|
| CH$_3$ | CH$_3$ | 200–201 |
| CH$_3$O | CH$_3$O | 183–185 |
| CH$_3$O | CH$_3$ | |
| Cl | CH$_3$O | |
| C$_2$H$_5$ | CH$_3$O | |
| CH$_3$OCH$_2$ | CH$_3$O | |
| CH$_3$CH$_2$CH$_2$O | CH$_3$O | 121–124 |
| (CH$_3$)$_2$CHO | CH$_3$O | |
| CH$_3$S | CH$_3$O | 197–199 |
| (CH$_3$)$_2$CHO | CH$_3$ | |
| CH$_3$S | CH$_3$ | |
| CH$_3$CH$_2$O | CH$_3$ | |
| H | CH$_3$O | |
| CF$_3$ | CH$_3$O | |
| Br | CH$_3$O | |

TABLE I-B

| R$_3$ | X | Z | m.p. °C |
|---|---|---|---|
| CH$_3$ | CH$_3$O | CH$_3$ | 158–162 |
| CH$_3$ | CH$_3$O | CH$_3$O | 144–147 |
| CH$_3$ | CH$_3$OCH$_2$ | CH$_3$ | 147–150 |
| CH$_3$ | (CH$_3$)$_2$CHO | CH$_3$O | |
| CH$_3$ | CH$_3$CH$_2$CH$_2$O | CH$_3$O | |
| CH$_3$ | CH$_3$S | CH$_3$O | 191–193 |
| Cl | CH$_3$ | CH$_3$ | 185–187 |
| Cl | CH$_3$O | CH$_3$ | 174–178 |
| Cl | CH$_3$O | CH$_3$O | 188–189 |
| Cl | CH$_3$OCH$_2$ | CH$_3$ | 142–145 |
| Cl | CH$_3$CH$_2$O | CH$_3$ | 117–121 |
| Cl | CH$_3$CH$_2$O | CH$_3$O | 132–133 |
| I | CH$_3$ | CH$_3$ | |
| F | CH$_3$O | CH$_3$ | 168–172 |
| F | CH$_3$O | CH$_3$O | 169–175 |
| CF$_3$ | CH$_3$ | CH$_3$ | 172–174 |
| CF$_3$ | CH$_3$ | CH$_3$O | 165–167 |
| NO$_2$ | CH$_3$ | CH$_3$O | 178–181 dec. |
| NO$_2$ | CH$_3$O | CH$_3$O | 175–178 |

TABLE I-B-continued

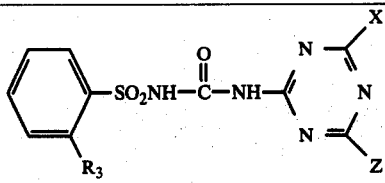

| R₃ | X | Z | m.p. °C |
|---|---|---|---|
| CH₃ | CH₃S | CH₃ | |
| CH₃ | H | CH₃ | |
| CH₃ | CH₃CH₂O | CH₃ | |
| CH₃ | (CH₃)₂CHO | CH₃ | |
| Cl | H | CH₃ | |
| Cl | CH₃S | CH₃ | |
| Cl | Cl | CH₃ | |
| Br | CH₃ | CH₃ | |
| Br | CH₃ | CH₃O | |
| Br | CH₃O | CH₃O | |
| NO₂ | CH₃ | CH₃ | |
| F | H | CH₃ | |
| F | CH₃S | CH₃ | |
| F | CH₃CH₂O | CH₃ | |
| F | (CH₃)₂CHO | CH₃ | |
| CH₃S | CH₃O | CH₃ | |
| F | CH₃CH₂O | CH₃O | |
| CH₃O | CH₃ | CH₃ | |
| C₂H₅SO₂ | H | CH₃ | |
| CH₃O | CH₃S | CH₃ | |
| CH₃O | CH₃CH₂O | CH₃ | |
| n-C₄H₉O | Cl | CH₃ | |
| CH₃O | CH₃O | CH₃ | |
| CH₃O | CH₃O | CH₃O | |
| C₂H₅ | CH₃ | CH₃ | |
| C₂H₅ | CH₃ | CH₃O | |
| C₂H₅ | CH₃O | CH₃O | |
| n-C₄H₉ | CH₃ | CH₃ | |
| (CH₃)₂CH | CH₃ | CH₃O | |
| (CH₃)₂CH | CH₃O | CH₃O | |
| n-C₃H₇ | CH₃O | CH₃O | |
| CN | CH₃O | CH₃O | |

TABLE I-C

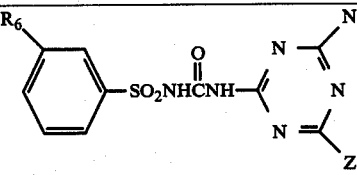

| R₆ | X | Z | m.p. |
|---|---|---|---|
| Cl | CH₃ | CH₃ | 190-191 |
| Cl | CH₃ | CH₃O | above 250 |
| Cl | CH₃O | CH₃O | 158-162 |
| CF₃ | CH₃ | CH₃ | |
| CH₃ | CH₃ | CH₃ | |
| CH₃ | CH₃ | CH₃O | |
| CH₃ | CH₃O | CH₃O | |
| CH₃ | H | CH₃ | |
| CH₃ | CH₃CH₂O | CH₃ | |
| CH₃ | CH₃CH₂O | CH₃O | |
| Cl | CH₃S | CH₃O | |
| Br | CH₃ | CH₃ | |
| Br | CH₃ | CH₃O | |
| Br | CH₃O | CH₃O | |
| NO₂ | CH₃ | CH₃ | |
| NO₂ | CH₃O | CH₃ | |
| NO₂ | CH₃O | CH₃O | |
| CF₃ | CH₃O | CH₃O | |
| CF₃ | CH₃O | CH₃ | |
| CH₃SO₂ | CH₃O | CH₃O | |
| CH₃CH₂SO₂ | CH₃O | CH₃O | |
| I | CH₃ | CH₃ | |
| F | CH₃O | CH₃ | |
| F | C₂H₅O | CH₃ | |
| F | C₂H₅O | CH₃O | |
| F | CH₃S | CH₃O | |
| F | (CH₃)₂CHO | CH₃O | |
| Cl | H | CH₃ | |
| Br | H | CH₃O | |
| CH₃O | CH₃ | CH₃ | |
| CH₃O | CH₃O | CH₃ | |
| CH₃O | CH₃O | CH₃O | |
| CH₃O | C₂H₅O | CH₃ | |
| CH₃O | C₂H₅O | CH₃O | |

TABLE I-C-continued

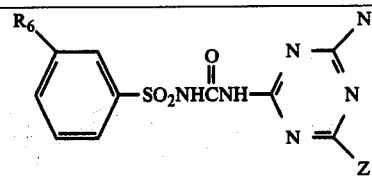

| R₆ | X | Z | m.p. |
|---|---|---|---|
| CH₃O | (CH₃)₂CHO | CH₃O | |
| n-C₄H₉O | H | CH₃O | |
| CH₃O | H | CH₃ | |
| CH₃ | CH₃ | CH₃ | |
| C₂H₅ | CH₃O | CH₃ | |
| CN | H | CH₃ | |
| CH₃S | CH₃O | CH₃O | |
| C₂H₅ | CH₃S | CH₃O | |
| n-C₄H₉ | CH₃ | CH₃ | |
| (CH₃)₂CH | CH₃ | CH₃O | |
| (CH₃)₂CH | CH₃O | CH₃O | |
| n-C₃H₇ | CH₃ | CH₃ | |

TABLE I-D

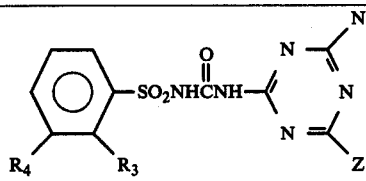

| R₃ | R₄ | X | Z | m.p. |
|---|---|---|---|---|
| Cl | Cl | CH₃ | CH₃ | 130-140 |
| Cl | Cl | CH₃ | CH₃O | 182-184 |
| Cl | Cl | CH₃O | CH₃O | 192-193 |
| F | Cl | CH₃ | CH₃ | 171-175 |
| F | Cl | CH₃ | CH₃O | 190-191 |
| F | Cl | CH₃O | CH₃O | 275 |
| Cl | CH₃ | CH₃ | CH₃ | 188-189 |
| Cl | CH₃ | CH₃ | CH₃O | 187 |
| Cl | CH₃ | CH₃O | CH₃O | 148-151 |
| CH₃O | Cl | CH₃O | CH₃O | 178 |
| CH₃O | Cl | CH₃ | CH₃O | |
| CH₃O | Cl | CH₃ | CH₃ | |
| CH₃O | Cl | CH₃S | CH₃O | |
| CH₃ | Cl | CH₃ | CH₃ | |
| CH₃ | Cl | CH₃ | CH₃O | |
| CH₃ | Cl | CH₃O | CH₃O | |
| CH₃ | F | CH₃ | CH₃ | |
| CH₃ | F | CH₃ | CH₃O | |
| CH₃ | F | CH₃O | CH₃O | |
| F | CH₃ | CH₃ | CH₃ | |
| F | CH₃ | CH₃ | CH₃O | |
| F | CH₃ | CH₃O | CH₃O | |
| F | F | CH₃S | CH₃O | |
| CH₃ | CH₃ | CH₃ | CH₃ | |
| CH₃ | CH₃ | CH₃ | CH₃O | |
| F | Cl | CH₃O | CH₃ | |
| F | H | CH₃O | CH₃ | |
| F | F | CH₃O | CH₃O | |
| F | F | CH₃ | CH₃O | |
| F | F | CH₃ | CH₃ | |
| CH₃ | CH₃ | CH₃O | CH₃ | |
| CH₃O | CH₃ | CH₃ | CH₃ | |
| CH₃O | F | CH₃ | CH₃ | |
| CH₃O | F | CH₃O | CH₃O | |
| CH₃ | Br | CH₃O | CH₃O | |
| Cl | Br | CH₃O | CH₃O | |
| C₂H₅ | Cl | CH₃ | CH₃O | |

TABLE I-E

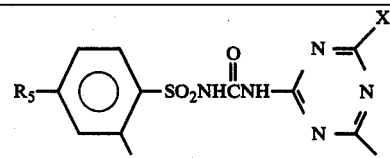

| R₃ | R₅ | X | Z | m.p. |
|---|---|---|---|---|
| Cl | Cl | CH₃O | CH₃O | 182-190 |
| Cl | Cl | CH₃ | CH₃O | |

TABLE I-E-continued

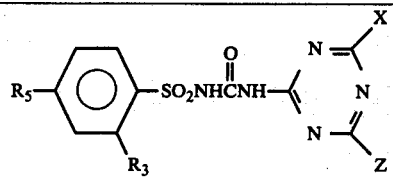

| R₃ | R₅ | X | Z | m.p. |
|---|---|---|---|---|
| Cl | Cl | CH₃ | CH₃ | |
| F | F | CH₃O | CH₃O | |
| F | F | CH₃ | CH₃O | |
| Cl | F | CH₃ | CH₃O | |
| Cl | F | CH₃ | CH₃ | |
| CH₃ | F | CH₃ | CH₃ | |
| CH₃ | F | CH₃O | CH₃O | |
| F | Cl | CH₃O | CH₃O | |
| F | Br | CH₃O | CH₃O | |
| CH₃ | CH₃O | CH₃ | CH₃O | |
| CH₃ | CH₃ | CH₃O | CH₃O | |
| CH₃ | Cl | CH₃O | CH₃O | |
| CH₃O | Cl | CH₃ | CH₃ | |
| CH₃ | F | CH₃ | CH₃ | |
| CH₃ | F | CH₃O | CH₃O | |

TABLE I-F

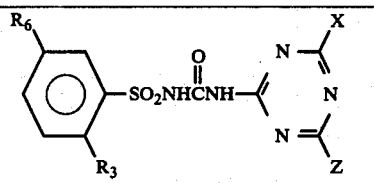

| R₃ | R₆ | X | Z | m.p. |
|---|---|---|---|---|
| Cl | Cl | CH₃ | CH₃ | 190–192 |
| Cl | Cl | CH₃ | CH₃O | 186–188 |
| Cl | Cl | CH₃O | CH₃O | 185–188 |
| Cl | Cl | CH₃CH₂O | CH₃ | 155–159 |
| Cl | Cl | CH₃CH₂O | CH₃O | 147–149 |
| CH₃ | CH₃ | CH₃ | CH₃ | |
| CH₃ | CH₃ | CH₃ | CH₃O | 160–163 |
| CH₃ | CH₃ | CH₃O | CH₃O | 169–173 |
| CH₃O | Cl | CH₃ | CH₃ | |
| CH₃O | Cl | CH₃ | CH₃O | 174–179 |
| CH₃O | Cl | CH₃O | CH₃O | 165 |
| CH₃O | Cl | CH₃CH₂O | CH₃ | 183–183.5 |
| CH₃O | F | CH₃O | CH₃O | 201–203 |
| F | Cl | CH₃O | CH₃O | |
| F | Cl | CH₃ | CH₃ | |
| F | F | CH₃ | CH₃ | 164–165 |
| F | F | CH₃ | CH₃O | |
| F | F | CH₃O | CH₃O | 206–208 |
| Cl | F | CH₃O | CH₃O | |
| Cl | F | CH₃ | CH₃ | |
| Cl | CH₃O | CH₃ | CH₃O | 176 |
| Cl | CH₃O | CH₃O | CH₃O | 201 |
| Cl | CH₃O | CH₃ | CH₃ | |
| Cl | CF₃ | CH₃ | CH₃O | 177–178 |
| Cl | CF₃ | CH₃O | CH₃O | 165–167 |
| Cl | NO₂ | CH₃ | CH₃ | 142–144 |
| Cl | NO₂ | CH₃ | CH₃O | |
| Cl | NO₂ | CH₃O | CH₃O | 168–174 |
| CH₃ | CH₃O | CH₃ | CH₃ | |
| CH₃ | CH₃O | CH₃O | CH₃O | |
| CH₃O | CH₃ | CH₃O | CH₃O | |
| CH₃O | CH₃ | CH₃ | CH₃ | |
| Cl | CH₃ | CH₃ | CH₃ | |
| Cl | CH₃ | CH₃O | CH₃O | |
| F | CH₃ | CH₃ | CH₃ | 180–182 |
| F | CH₃ | CH₃ | CH₃O | 185–186 |
| F | CH₃ | CH₃O | CH₃O | 191–192 |
| CH₃ | F | CH₃ | CH₃ | 201–205 |
| CH₃ | F | CH₃O | CH₃O | |
| CH₃ | F | CH₃O | CH₃O | 183–184 |
| F | CH₃ | (CH₃)₂CHO | CH₃O | |
| F | CH₃O | CH₃ | CH₃ | |
| F | CH₃O | CH₃ | CH₃O | |
| F | CH₃O | CH₃O | CH₃O | |
| CH₃ | CF₃ | CH₃ | CH₃ | |
| CH₃ | CF₃ | CH₃O | CH₃O | |
| CH₃ | (CH₃)₂CH | CH₃O | CH₃O | |
| F | CF₃ | CH₃ | CH₃ | |
| F | CF₃ | CH₃O | CH₃O | |
| CH₃ | Br | CH₃O | CH₃ | |
| Cl | Br | CH₃ | CH₃ | |

TABLE I-F-continued

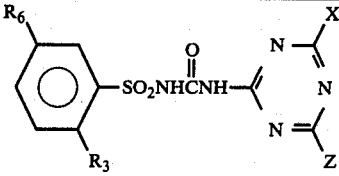

| R₃ | R₆ | X | Z | m.p. |
|---|---|---|---|---|
| CH₃ | CH₃SO₂ | CH₃O | CH₃O | |
| CH₃O | NO₂ | CH₃S | CH₃O | |
| Br | F | Cl | CH₃ | |
| CH₃O | (CH₃)₂CH | Br | CH₃O | |
| (CH₃)₂CH | CH₃O | CH₃S | CH₃O | |
| F | CH₃ | H | CH₃ | |
| CH₃ | NO₂ | CH₃ | CH₃O | 190–191 |
| CH₃ | NO₂ | CH₃O | CH₃O | 142–145 |
| CH₃ | NO₂ | CH₃ | CH₃ | |
| CH₃ | (CH₃)₂CH | CH₃ | CH₃ | 167 |
| CH₃ | (CH₃)₂CH | CH₃ | CH₃O | 115 |
| CH₃ | (CH₃)₂CH | CH₃O | CH₃O | 135 |
| CH₃CH₂O | Cl | CH₃ | CH₃ | 179–181 |
| CH₃CH₂O | CH₃CH₂O | CH₃ | CH₃ | 134–136 |
| CH₃CH₂O | CH₃CH₂O | CH₃ | CH₃O | 187–188 |
| CH₃ | Cl | CH₃ | CH₃ | 189–191 |
| CH₃ | Cl | CH₃O | CH₃O | |
| CH₃ | Cl | CH₃O | CH₃O | |
| Cl | CH₃ | CH₃ | CH₃ | |
| Cl | CH₃ | CH₃ | CH₃O | |
| Cl | CH₃ | CH₃O | CH₃O | |
| Br | Br | CH₃ | CH₃ | 204–205 |
| Br | Br | CH₃ | CH₃O | 178–180 |
| Br | Br | CH₃O | CH₃O | above 275 |
| CH₃O | CH₃O | CH₃ | CH₃ | 144–150 |
| CH₃O | CH₃O | CH₃O | CH₃O | 187–205 (dec) |
| CH₃O | CH₃O | CH₃O | CH₃O | 187–188 |
| CH₃O | CH₃O | CH₃CH₂O | CH₃ | 96–100 |
| CH₃O | CH₃O | CH₃CH₂O | CH₃O | 138–144 |

TABLE I-G

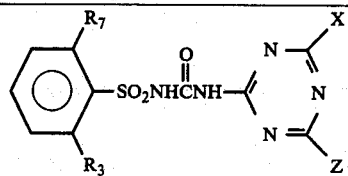

| R₃ | R₇ | X | Z | m.p. |
|---|---|---|---|---|
| Cl | Cl | CH₃ | CH₃ | 142–158 |
| Cl | Cl | CH₃ | CH₃O | 203–206 |
| Cl | Cl | CH₃O | CH₃O | 205–208 |
| Cl | Br | CH₃OCH₂ | CH₃ | |
| Cl | C₂H₅ | CH₃ | CH₃ | |
| Cl | CH₃ | CH₃ | CH₃O | 171–172 |
| Cl | CH₃ | CH₃O | CH₃O | 173–176 |
| F | F | CH₃ | CH₃ | 192–193 |
| F | F | CH₃ | CH₃O | 213–215 |
| F | F | CH₃O | CH₃O | 275 |
| Cl | CH₃O | CH₃O | CH₃O | |
| Cl | C₂H₅O | CH₃O | CH₃O | |

TABLE I-H

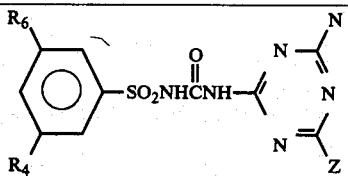

| R₄ | R₆ | X | Z | m.p. |
|---|---|---|---|---|
| Cl | Cl | CH₃ | CH₃ | 210–213 |
| Cl | Cl | CH₃O | CH₃O | 207 |
| CH₃ | CH₃ | CH₃O | CH₃ | |
| CH₃ | CH₃ | CH₃O | CH₃O | |
| CH₃ | CH₃ | CH₃ | CH₃ | |
| CH₃ | Cl | CH₃ | CH₃ | |
| CH₃ | Cl | CH₃O | CH₃ | |
| CH₃ | Cl | CH₃O | CH₃O | |
| CH₃ | F | CH₃O | CH₃O | |
| CH₃ | F | CH₃ | CH₃O | |

TABLE I-H-continued

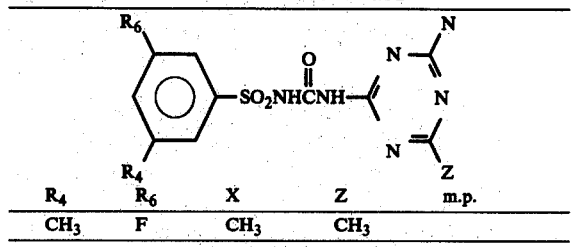

| R4 | R6 | X | Z | m.p. |
|---|---|---|---|---|
| CH3 | F | CH3 | CH3 | |

TABLE I-I

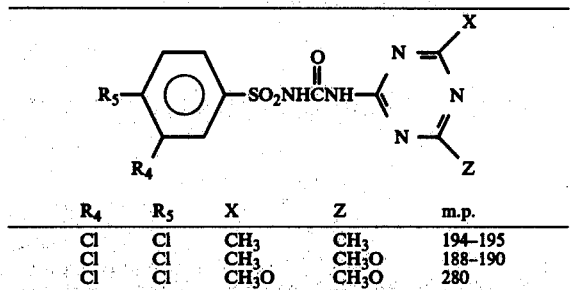

| R4 | R5 | X | Z | m.p. |
|---|---|---|---|---|
| Cl | Cl | CH3 | CH3 | 194–195 |
| Cl | Cl | CH3 | CH3O | 188–190 |
| Cl | Cl | CH3O | CH3O | 280 |

TABLE I-J

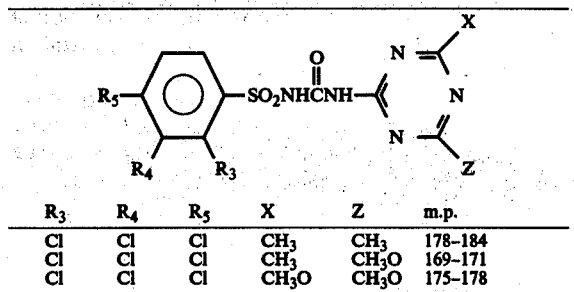

| R3 | R4 | R5 | X | Z | m.p. |
|---|---|---|---|---|---|
| Cl | Cl | Cl | CH3 | CH3 | 178–184 |
| Cl | Cl | Cl | CH3 | CH3O | 169–171 |
| Cl | Cl | Cl | CH3O | CH3O | 175–178 |

TABLE I-K

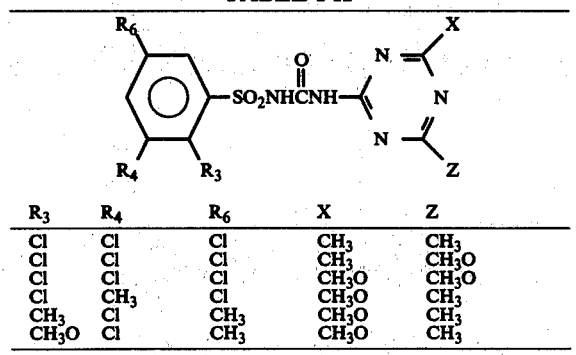

| R3 | R4 | R6 | X | Z |
|---|---|---|---|---|
| Cl | Cl | Cl | CH3 | CH3 |
| Cl | Cl | Cl | CH3 | CH3O |
| Cl | Cl | Cl | CH3O | CH3O |
| Cl | CH3 | Cl | CH3O | CH3 |
| CH3 | Cl | CH3 | CH3 | CH3 |
| CH3O | Cl | CH3 | CH3 | CH3 |

TABLE I-L

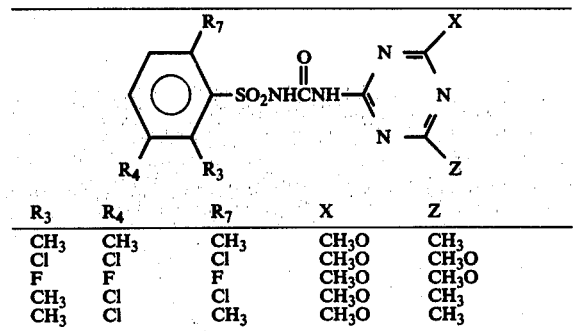

| R3 | R4 | R7 | X | Z |
|---|---|---|---|---|
| CH3 | CH3 | CH3 | CH3O | CH3 |
| Cl | Cl | Cl | CH3O | CH3O |
| F | F | F | CH3O | CH3O |
| CH3 | Cl | Cl | CH3O | CH3 |
| CH3 | Cl | CH3 | CH3 | CH3 |

TABLE I-L-continued

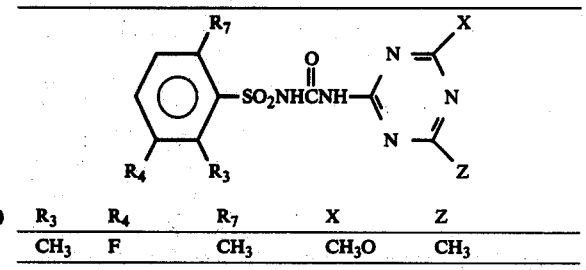

| R3 | R4 | R7 | X | Z |
|---|---|---|---|---|
| CH3 | F | CH3 | CH3O | CH3 |

TABLE I-M

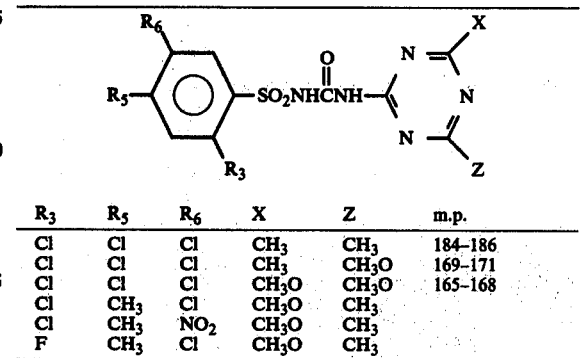

| R3 | R5 | R6 | X | Z | m.p. |
|---|---|---|---|---|---|
| Cl | Cl | Cl | CH3 | CH3 | 184–186 |
| Cl | Cl | Cl | CH3 | CH3O | 169–171 |
| Cl | Cl | Cl | CH3O | CH3O | 165–168 |
| Cl | CH3 | Cl | CH3O | CH3 | |
| Cl | CH3 | NO2 | CH3O | CH3 | |
| F | CH3 | Cl | CH3O | CH3 | |

TABLE I-N

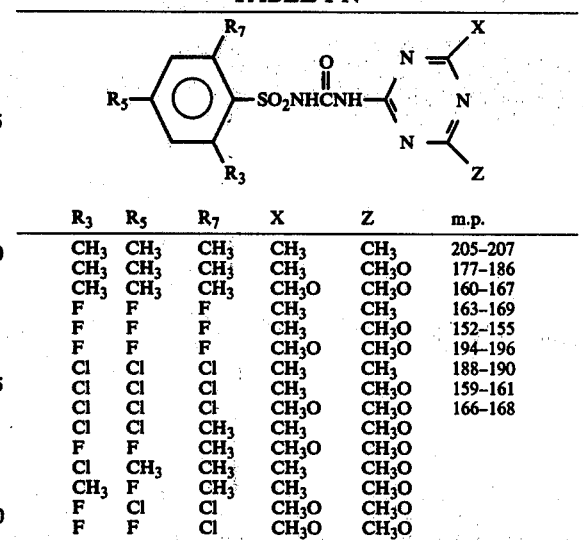

| R3 | R5 | R7 | X | Z | m.p. |
|---|---|---|---|---|---|
| CH3 | CH3 | CH3 | CH3 | CH3 | 205–207 |
| CH3 | CH3 | CH3 | CH3 | CH3O | 177–186 |
| CH3 | CH3 | CH3 | CH3O | CH3O | 160–167 |
| F | F | F | CH3 | CH3 | 163–169 |
| F | F | F | CH3 | CH3O | 152–155 |
| F | F | F | CH3O | CH3O | 194–196 |
| Cl | Cl | Cl | CH3 | CH3 | 188–190 |
| Cl | Cl | Cl | CH3 | CH3O | 159–161 |
| Cl | Cl | Cl | CH3O | CH3O | 166–168 |
| F | F | CH3 | CH3O | CH3O | |
| Cl | CH3 | CH3 | CH3 | CH3 | |
| CH3 | F | CH3 | CH3 | CH3 | |
| F | F | Cl | CH3O | CH3O | |
| F | F | Cl | CH3O | CH3O | |

TABLE I-O

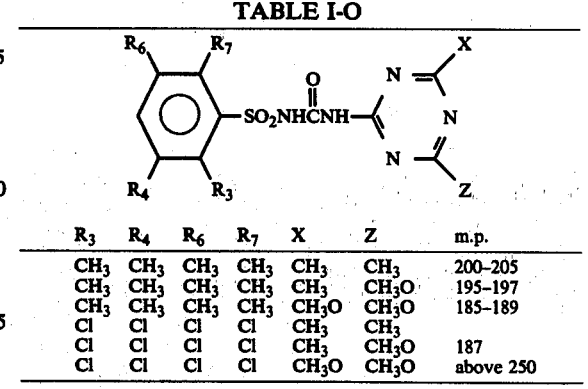

| R3 | R4 | R6 | R7 | X | Z | m.p. |
|---|---|---|---|---|---|---|
| CH3 | CH3 | CH3 | CH3 | CH3 | CH3 | 200–205 |
| CH3 | CH3 | CH3 | CH3 | CH3 | CH3O | 195–197 |
| CH3 | CH3 | CH3 | CH3 | CH3O | CH3O | 185–189 |
| Cl | Cl | Cl | Cl | CH3 | CH3 | |
| Cl | Cl | Cl | Cl | CH3 | CH3O | 187 |
| Cl | Cl | Cl | Cl | CH3O | CH3O | above 250 |

EXAMPLE 4

N-[(4-methoxy-6-methyl-1,3,5-triazin-2-yl)-aminocarbonyl]-2-thiophensulfonamide

To a suspension of 14.0 g of 2-amino-4-methoxy-6-methyl-1,3,5-triazine in 300 ml. of acetonitrile was added, dropwise, 19 g of thiophene-2-sulfonyl isocyanate. After stirring for six hours, the mixture was filtered to yield the desired solid product melting at 182°–184° C.

By using the procedure of Example 4 with equivalent amounts of the appropriate amino-1,3,5-triazine derivative and sulfonyl isocyanate the compounds of Table II can be prepared.

TABLE II-A

| $R_9$ | $R_{10}$ | X | Z | m.p. |
|---|---|---|---|---|
| Cl | Cl | $CH_3$ | $CH_3$ | 127–133 |
| Cl | Cl | $CH_3$ | $CH_3O$ | 165–171 |
| Cl | Cl | $CH_3O$ | $CH_3O$ | 181–184 |
| $CH_3$ | $CH_3$ | $CH_3$ | $CH_3O$ | |
| $CH_3$ | $CH_3$ | $CH_3O$ | $CH_3O$ | |
| Br | Br | $CH_3O$ | $CH_3O$ | |
| H | H | $CH_3$ | $CH_3O$ | |

TABLE II-B

| $R_8$ | X | Z | Q | m.p. |
|---|---|---|---|---|
| H | $CH_3$ | $CH_3$ | S | 174–176 |
| H | $CH_3$ | $CH_3O$ | S | 182–184 |
| H | $CH_3O$ | $CH_3O$ | S | 191–192 |
| $CH_3$ | $CH_3$ | $CH_3O$ | S | |
| $CH_3$ | $CH_3O$ | $CH_3O$ | S | |
| $CH_3$ | $CH_3CH_2O$ | $CH_3O$ | S | |
| Cl | $CH_3$ | $CH_3$ | S | 192–195 |
| Br | $CH_3$ | $CH_3O$ | S | |
| Cl | $CH_3O$ | $CH_3O$ | S | 193–195 |
| H | $CH_3$ | $CH_3O$ | O | |
| H | $CH_3O$ | $CH_3O$ | O | |

EXAMPLE 5

N-[(4,6-Dimethoxy-1,3,5-triazin-2-yl)aminocarbonyl]-1-naphthalenesulfonamide

To a suspension of 16 g of 2-amino-4,6-dimethoxy-1,3,5-triazine in 400 ml of acetonitrile was added 23.3 g of 1-naphthalenesulfonyl isocyanate dropwise with stirring. The mixture was stirred for 14 hours and the resultant solid product removed by filtration. After washing with ethyl ether the product melted at 171°–172° C.

By using the procedure of Example 5 and substituting equivalent amounts of the appropriate amino-1,3,5-triazine and sulfonyl isocyanate, the following compounds of Table III can be prepared.

TABLE III

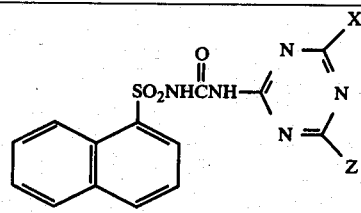

| X | Z | m.p. |
|---|---|---|
| $CH_3$ | $CH_3$ | 179–183 |
| $CH_3$ | $CH_3O$ | 186–188 |
| $CH_3O$ | $CH_3O$ | 171–172 |
| $CH_3OCH_2$ | $CH_3$ | |

EXAMPLE 6

N-[(4,6-Dimethoxy-1,3,5-triazin-2-yl)aminothioxomethyl]benzenesulfonamide

A mixture containing 20 g of benzenesulfonyl isothiocyanate, 15.6 g of 2-amino-4,6-dimethoxy-1,3,5-triazine, 250 ml of acetonitrile and a catalytic amount of dibutyltin dilaurate was stirred for 24 hours. After filtration to remove unreacted triazine, the evaporation of the acetonitrile yielded a gummy residue. Trituration of this material with ethyl ether resulted in the precipitation of the desired compound, which was isolated by filtration and melted at 148°–150° C.

By using the procedure of Example 6 with an equivalent amount of the appropriate sulfonyl isothiocyanate and aminotriazine, the compounds of Table IV can be prepared.

TABLE IV $$R_1SO_2NHCNHR_2$$
with C=S

| $R_1$ | $R_2$ |
|---|---|
| phenyl | 4,6-dimethyl-1,3,5-triazin-2-yl |
| phenyl | 4,6-dimethoxy-1,3,5-triazin-2-yl |
| 2-methylphenyl | 4,6-dimethoxy-1,3,5-triazin-2-yl |
| 2-fluorophenyl | 4,6-dimethoxy-1,3,5-triazin-2-yl |

TABLE IV-continued $$R_1SO_2NHCNHR_2 \quad (\overset{S}{\|})$$

| $R_1$ | $R_2$ |
|---|---|
| 2-Br-phenyl | 4,6-dimethoxy-1,3,5-triazin-2-yl |
| 2-Cl-phenyl | 4,6-dimethoxy-1,3,5-triazin-2-yl |
| 2-F-phenyl | 4,6-dimethoxy-2-methyl-pyrimidin-2-yl (4-methyl-6-methoxy-1,3,5-triazin-2-yl) |
| 2-Cl-phenyl | 4-methyl-6-methoxy-1,3,5-triazin-2-yl |
| 2-CH$_3$-phenyl | 4-methyl-6-methoxy-1,3,5-triazin-2-yl |
| 2-OCH$_3$-phenyl | 4-methyl-6-methoxy-1,3,5-triazin-2-yl |
| 2-C$_2$H$_5$-phenyl (2-Br) | 4-methyl-6-methoxy-1,3,5-triazin-2-yl |
| 2,5-diCl-phenyl | 4,6-dimethoxy-1,3,5-triazin-2-yl |
| 2,4-diCH$_3$-phenyl | 4,6-dimethoxy-1,3,5-triazin-2-yl |
| 2-Cl-4-OCH$_3$-phenyl | 4,6-dimethoxy-1,3,5-triazin-2-yl |
| 2,4-diOCH$_3$-phenyl (4-OCH$_3$, 2-OCH$_3$) | 4,6-dimethoxy-1,3,5-triazin-2-yl |
| 2,3-diCl-phenyl | 4,6-dimethoxy-1,3,5-triazin-2-yl |
| 2,5-diCl-phenyl | 4-methyl-6-methoxy-1,3,5-triazin-2-yl |
| 2,4-diCH$_3$-phenyl | 4-methyl-6-methoxy-1,3,5-triazin-2-yl |
| 2-OCH$_3$-4-OCH$_3$-phenyl | 4-methyl-6-methoxy-1,3,5-triazin-2-yl |
| 2-Cl-4-OCH$_3$-phenyl | 4-methyl-6-methoxy-1,3,5-triazin-2-yl |

TABLE IV-continued $$R_1SO_2NHCNHR_2 \text{ (C=S)}$$

| $R_1$ | $R_2$ |
|---|---|
| thiophene | -C(CH$_3$)=N-C(OCH$_3$)=N-N= (triazine with CH$_3$ and OCH$_3$) |
| thiophene | -C(OCH$_3$)=N-C(OCH$_3$)=N-N= (triazine with two OCH$_3$) |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of a) about 0.1% to 20% surfactants(s) and b) about 1% to 99.9% solid or liquid diluent(s). More specifically, they will contain these ingredients in the following approximate proportions:

TABLE V

|  | Active Ingredient | Diluent(s) | Surfactant(s) |
|---|---|---|---|
| Wettable Powders | 20–90 | 0–74 | 1–10 |
| Oil Suspensions, Emulsions, Solutions (including Emulsifiable Concentrates) | 3–50 | 40–95 | 0–15 |
| Aqueous Suspensions | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foam, caking, corrosion, microbiological growth, etc.

The methods of making such compositions are well know. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made for spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Ed., McGraw-Hill, New York, 1963, pp. 8–59 ff.

For further information regarding the art of formulation, see for example:

H. M. Loux, U.S. Pat. No. 3,235,361, February 15, 1966, Col. 6, line 16 through Col. 7, line 19 and Examples 10 through 41.

R. W. Luckenbaugh, U.S. Pat. No. 3,309,192, March 14, 1967, Col. 5, line 43 through Col. 7, line 62 and Examples 8, 12, 15, 39, 41, 52, 53, 58, 132, 138–140, 1-62–164, 166, 167, 169–182.

H. Gysin and E. Knusli, U.S. Pat. No. 2,891,855, June 23, 1959, Col. 3, line 66 through Col. 5, line 17 and Examples 1–4.

G. C. Klingman, "Weed Control as a Science", John Wiley & Sons, Inc., New York, 1961, pp. 81–96.

J. D. Fryer and S.A. Evans, "Weed Control Handbook", 5th Ed., Blackwell Scientific Publications, Oxford, 1968, pp. 101–103.

In the following examples, all parts are by weight unless otherwise indicated.

EXAMPLE 7

| Wettable powder | |
|---|---|
| N-[4,6-dimethoxy-1,3,5-triazin-2-yl)aminocarbonyl]benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended and packaged.

EXAMPLE 8

| Wettable Powder | |
|---|---|
| N-[(4,6-dimethyl-1,3,5-triazin-2-yl)-aminocarbonyl]benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 9

| Granule | |
|---|---|
| wettable powder of Example 8 | 5% |
| attapulgite granules | 95% |
| (U.S.S. 20-40 mesh; 0.84-0.42 mm) | |

A slurry of wettable powder containing ≈25% solids is sprayed on the surface of attapulgite granules in a double-cone blender. The granules are dried and packaged.

EXAMPLE 10

| Extruded Pellet | |
|---|---|
| N-[(4-methoxy-6-methyl-1,3,5-triazin-2-yl)-aminocarbonyl]-2-chloro-benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S.No. 20 sieve (0.84 mm openings). The granules held on a U.S.S.No. 40 sieve (0.42 mm openings) may be packaged for use and the fines recycled.

EXAMPLE 11

| Oil Suspension | |
|---|---|
| N-[(4,6-dimethoxy-1,3,5-triazin-2-yl)-aminocarbonyl]-2-chloro-5-methoxybenzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting suspension may be applied directly, but preferably after being extended with oils or emulsified in water.

EXAMPLE 12

| Wettable Powder | |
|---|---|
| N-[(4,6-dimethoxy-1,3,5-triazin-2-yl)-aminocarbonyl]-2-chloro-benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer mill to produce particles essentially all below 100 microns, the material is reblended and sifted through a U.S.S.No. 50 sieve (0.3 mm opening) and packaged.

EXAMPLE 13

| Oil Suspension | |
|---|---|
| N-[(4,6-dimethoxy-1,3,5-triazin-2-yl)-aminocarbonyl]-benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 3 microns. The product can be used directly, extended with oils, or emulsified in water.

EXAMPLE 14

| High Strength Concentrate | |
|---|---|
| N-[(4,6-dimethoxy-1,3,5-triazin-2-yl)-aminocarbonyl]benzenesulfonamide | 99% |
| silica aerogel | 0.5% |
| synthetic amorphous silica | 0.5% |

The ingredients are blended and ground in a hammer mill to produce a material essentially all passing a U.S.S.No. 50 screen (0.3 mm opening). The concentrate may be formulated further if necessary.

EXAMPLE 15

| Low Strength Granule | |
|---|---|
| N-[(4-methoxy-6-methyl-1,3,5-triazin-2-yl)-aminocarbonyl]-2-chloro-5-methoxybenzenesulfonamide | 1% |
| N,N-dimethylformamide | 9% |
| attapulgite granules | 90% |
| (U.S.S. 20-40 mesh). | |

The active ingredient is dissolved in the solvent and the solution is sprayed upon dedusted granules in a rotating blender. After spraying of the solution has been completed, the blender is allowed to run for a short period and then the granules are packaged.

EXAMPLE 16

| Aqueous Suspension | |
|---|---|
| N-[(4,6-dimethyl-1,3,5-triazin-2-yl)-aminocarbonyl]-benzenesulfonamide | 40% |
| Polyacrylic acid thickener | 0.3% |
| Dodecylphenol polyethylene glycol ether | 0.5% |
| Disodium phosphate | 1% |
| Monosodium phosphate | 0.5% |
| Polyvinyl alcohol | 1.0% |
| Water | 56.7% |

The ingredients are blended and ground together in a sand mill to produce particles essentially all under 5 microns in size.

EXAMPLE 17

| Solution | |
|---|---|
| N-[(4-methoxy-6-methyl-1,3,5-triazin-2-yl)-aminocarbonyl]-2-chloro-benzenesulfonamide, sodium salt | 5% |
| water | 95% |

The salt is added directly to the water with stirring to produce the solution, which may then be packaged for use.

EXAMPLE 18

| Granule | |
|---|---|
| N-[4,6-dimethoxy-1,3,5-triazin-2-yl)-aminocarbonyl]-2,5-dimethoxy-benzenesulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 19

| Low Strength Granule | |
|---|---|
| N-[(4-methoxy-6-methyl-1,3,5-triazin-2-yl)-aminocarbonyl]-2-chlorobenzenesulfonamide | 0.1% |
| attapulgite granules (U.S.S. 20-40 mesh) | 99.9% |

The active ingredient is dissolved in a solvent and the solution is sprayed upon dedusted granules in a double cone blender. After spraying of the solution has been completed, the material is warmed to evaporate the solvent. The material is allowed to cool and then packaged.

EXAMPLE 20

| Wettable Powder | |
|---|---|
| N-[(4-methoxy-6-methyl-1,3,5-triazin-2-yl)aminocarbonyl]-2-chloro-5-methoxybenzenesulfonamide | 95% |
| dioctyl sodium sulfosuccinate | 0.1% |
| synthetic fine silica | 4.9% |

The ingredients are blended and ground in a hammer-mill to produce particles essentially all below 100 microns. The material is sifted through a U.S.S. No. 50 screen and then packaged.

EXAMPLE 21

| Wettable Powder | |
|---|---|
| N-[(4-methoxy-6-methyl-1,3,5-triazin-2-yl)aminocarbonyl]-2-chlorobenzene-sulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

The compounds of Formula I can be formulated using the procedures of Examples 7-21.

UTILITY

The compounds of Formula I are useful as herbicides. They may be applied either pre- or postemergence for the control of undesired vegetation in noncrop areas or for selective weed control in certain crops, e.g., wheat. Some of these compounds are useful for the pre- and/or postemergence control of nutsedge. By properly selecting rate and time of application, compounds of this invention may be used to modify plant growth beneficially.

The precise amount of the compound of Formula I to be used in any given situation will vary according to the particular end result desired, the use involved, the weeds to be controlled, the soil type, the formulation and mode of application, weather conditions, etc. Since so many variables play a role, it is not possible to state a rate of application suitable for all situations. Broadly speaking, the compounds of this invention are used at levels of about 0.005 to 20 kg/ha with a preferred range of 0.01 to 10 kg/ha. The lower rates of the range will generally be selected for lighter soils, for selective weed control in crops, or in situations where maximum persistence is not necessary. Some of the compounds of Formula I can be used at very low rates for plant growth modification, but higher rates may also be useful, depending on factors such as the crop being treated, timing of treatment, etc.

The compounds of Formula I may be combined with other herbicides and are particularly useful in combination with 3-(3,4-dichlorophenyl)-1,1-dimethylurea, the triazines such as 2-chloro-4-(ethylamino)-6-(isopropylamino)-s-triazine, the uracils such as 5-bromo-3-sec-butyl-6-methyluracil, N-(phosponomethyl)glycine, 3-cyclohexyl-1-methyl-6-dimethylamino-s-triazine-2,4(1H,3H)-dione, N,N-dimethyl-2,2-diphenylacetamide, 2,4-dichlorophenoxyacetic acid (and closely related compounds), 4-chloro-2-butynyl-3-chlorophenyl-carbamate (Carbyne ®), diisopropylthiolcarbamic acid, ester with 2,3-dichloroallyl alcohol (Avadex ®), diisopropylthiolcarbamic acid, S-(2,3,3-trichloroallyl) ester (Avadex ®BW), ethyl-N-benzoyl-N-(3,4-dichlorophenyl)-2-aminopropionate (Suffix ®), 1,2-dimethyl-3,5-diphenylpyrazolium methyl-sulfate (Avenge ®), methyl(2-[4-(2,4-dichlorophenoxy)-phenoxy]-propanoate (Hoelon ®), 4-amino-6-tert-butyl-3-(methylthio)-1,2,4-triazin-5(4H)-one (Lexone ®), 3-(3,4-dichlorophenyl)-1-methoxy-1-methylurea (Lorox ®), 3-isopropyl-1H-2,1,3-benzothiodiazin-(4)-3H-one 2,2-dioxide, $\alpha,\alpha,\alpha$-trifluoro-2,6-dinitro-N,N-dipropyl-p-toluidine, 1,1'-dimethyl-4,4'-bipyridinium ion, monosodium methanearsonate, 2-chloro-2',6'-diethyl-(methoxymethyl) acetanilide, and 1,1-dimethyl-3-($\alpha,\alpha,\alpha$-trifluoro-m-tolyl)urea (Cotoran ®).

The activity of these compounds was discovered in greenhouse tests. The tests are described and the data resulting from them are shown below.

TEST PROCEDURE

Seeds of crabgrass (*Digitaria* sp.), barnyard-grass (*Echinochloa crusgalli*), wild oats (*Avena fatua*), *Cassia tora*, morningglory (*Impomoea* sp.), cocklebur (*Xanthium* sp.), sorghum, corn, soybean, rice, wheat and nutsedge tubers were planted in a growth medium and treated preemergence with the chemicals dissolved in a nonphytotoxic solvent. At the same time, cotton having five leaves (including cotyledonary ones), bush beans with the third trifoliolate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for 16 days, then all species were compared to controls and visually rated for response to treatment.

Ratings for compounds tested by this procedure are recorded in Table VI.

0 = no effect
& or 10 = maximum effect
B = burn
C = chlorosis or necrosis
D = defoliation
E = emergence inhibition
G = growth retardation
H = formative effects
I = increased green coloration
L = lodging
P = terminal bud kill
S = albinism
U = unusual pigmentation
6Y = abscised buds or flowers
%Z = fasciation
X = axillary stimulation
6F = delayed flowering
7F = change in flower pigment Table VI

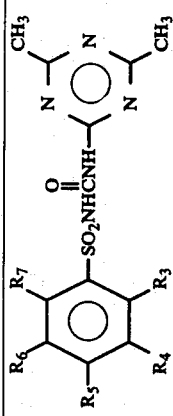

| R3 | R4 | R5 | R6 | R7 | Mode of Application | Rate Kg/Ha | BUSH BEAN | COTTON | SOR-GHUM | CORN | SOY-BEAN | WHEAT | WILD OATS | RICE | BARN-YARD GRASS | CRAB-GRASS | MORNING GLORY | COCK-LEBUR | CASSIA | NUT-SEDGE |
|---|---|---|---|---|---|---|---|---|---|---|---|---|---|---|---|---|---|---|---|---|
| H | Cl | H | Cl | H | Post | 0.4 | 3C 7G 6Y | 2C 2H 5G | 1C 5H | 6H | 1C 6G | | 0 | 4G | 0 | 0 | 1C | 4C 8G | | 0 |
| F | H | H | F | H | Post | 0.4 | 2C 8G 6Y | 5C 7G | 1C 6G 8G | 1C 8H 6G | 1C 2C 7G | 1C | 0 | 2C 8H 8G | 2C | 2G | 5G | 2C 7G 5C 9G | 3C | 1C 7G |
| | | | | | Pre | 0.4 | | | | | | 0 | 0 | | 0 | 0 | 1C 6G | | 2C | 0 |
| Cl | Cl | H | H | H | Post | 0.4 | 9C | 5C 9G | 1C 6G 9U 9H | 5G 9C 5C 9G | 9C 9H | 2C 8G 8G | 0 | 1C 6G 9C | 9H 1C 9H 7G | 4G 3G | 4G 3G | 5C 9G 1C 9G | &C 9G | 2C 5G 9G 2C 9G 7G | 1C 5G 4G |
| F | H | H | CH3 | H | Pre | 0.4 | 6D 8G 6Y | 1C 2H 6G | 2H 9G | 6G | 3H 9G | 1C | 0 | &E 1C 9G | 2C 5G | 2G | 5C 9G 9G | &C 9G | 2C 9G 0 | 2C 8G |
| | | | | | Post | 0.4 | | | 2H 8G | 0 | 1C 2H 3H | 0 | 2C | 9H | 0 | 0 | 1C | &C | 0 | 0 |
| H | Cl | Cl | H | H | Post | 0.4 | 1B 2H | 1C 3H | 3G 4G | 5G 0 | 0 2C 2H | 5G | 0 | 7G 4G | 0 1C | 0 | 9G 1C | 2C 9G 3H | 2C 1C | 0 1C |
| Cl | Cl | H | H | H | Pre | 2.0 | 3H 8G 6Y | 4C 9G | | | 2H 8G | | 2G | 0 | | 0 | | | | |
| | | | | | Post | 2.0 | | | 0 0 | 2G 2G | 0 2C 2H 5H | 0 | 0 | 0 | 1C 0 | 2C 0 | 5H 6H | 5H 7G | 0 2G | 0 0 |
| Cl | H | H | Cl | H | Pre | 2.0 | 3C 4H 6Y | 2C | 3G 8G | 1H 8G 5I | 0 1C 5G | 3G 5G 5X | 5G | 3G 5H | 0 9H | 2G 5G | 8G 1C 7G | 2C 9G 3H 8G 3C 9G | 0 2G | 0 1C 7G |
| H | H | H | H | H | Pre | 2.0 | 1C 7G 6Y | 1H 1C 8G | 8G | 9G | 1H 5G 2C 9G | 6G | 5G | &E 1C | 8G | 3G | 8G | &E | 5G | &E |
| Cl | H | H | H | H | Post | 0.4 | 9C | 9C | 9U 9H | 9C 9G | 2C 9G 9H | 2C 9G 7G | 1C 6G 3G | 9C &E | &C 1C 9G | 5C 9G 8G | &C | 9C | 9C | 9C |
| | | | | | Pre | 0.4 | | | | | | | | | | | | | | 8G |
| CH3 | CH3 | H | H | CH3 | Post | 0.4 | 2G | 2G | 0 | 0 | 8G | 0 | 0 | 2G | 8G | 0 | 8G | 0 | 5G | 0 |
| Cl | H | H | NO2 | H | Pre | 0.4 | 1C 8G 6F | 0 | 0 8G 2G | 2G 2H 0 | 1H 2G 0 | 0 4G 0 | 0 0 | 3G 5C 9H | 0 2C 1C 7H | 0 2C 1C 7H 0 | 8G 0 0 | 5H 0 0 | 8G 0 0 | 0 0 0 |
| F | F | F | H | F | Pre | 0.4 | 2G | 0 | | | 0 | 0 | | | | | | | | |
| | | | | | Post | 0.4 | 3C | 0 | 0 | 0 | 0 | 0 | 0 | 0 | 0 | 0 | 1G | 0 | 0 | 3G |

Table VI—continued

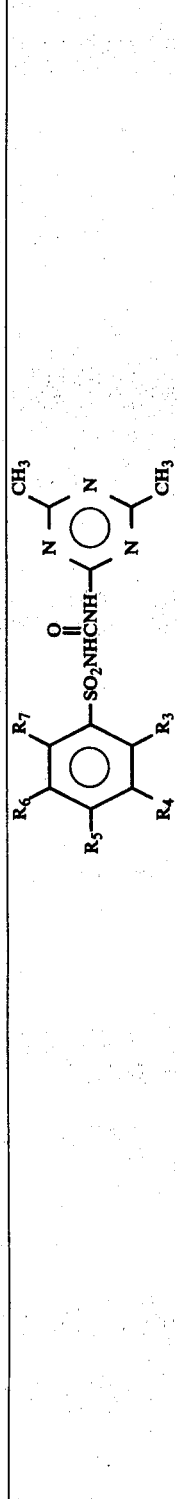

| R3 | R4 | R5 | R6 | R7 | Mode of Application | Rate Kg/Ha | BUSH BEAN | COTTON | SOR-GHUM | CORN | SOY-BEAN | WHEAT | WILD OATS | RICE | BARN-YARD-GRASS | CRAB-GRASS | MORNING GLORY | COCK-LEBUR | CASSIA | NUT-SEDGE |
|---|---|---|---|---|---|---|---|---|---|---|---|---|---|---|---|---|---|---|---|---|
| Cl | H | Cl | H | Cl | Pre | 0.4 | 3C | 5C | 0 | 2G | 1H | 2G | 0 | 2G | 2G | 3G | 0 | 0 | 0 | &E |
|  |  |  |  |  | Post | 0.4 | 8G 6Y | 6G | 2G | 2G | 3H 6G | | 0 | 0 | 1C | 0 | 2C | 2G | 1H | 3G |
| H | Cl | H | H | H | Pre | 0.4 | 2C | 3S | 0 | 4G | 2G | 2G | 0 | 0 | 1H | 2G | 3G | 4G | 0 | &E |
|  |  |  |  |  | Post | 0.4 | 7G 6Y | 7G | 1C 8G | 5G | 1C 3G | 0 | 0 | 1C 8G | 0 | 0 | 7G | &P 8G | 1C | 1C 5G |
| H | CF3 | H | H | H | Pre | 0.4 | | | 4G | 1C | 1C | 0 | 2G | 2C 9H | 0 | 2G | 8G | 8H | 5G | 3G |
|  |  |  |  |  | Post | 0.4 | | | 1C | 7G 0 | | | 0 | | 1C | 0 | 2C 6G | 2C 7G 6F 3C | 2C | 1C |
| H | H | H | H | H | Pre | 2.0 | 2H 3C 6Y | 1B 3C 2H | 3G | 1C 5G 5G | 1H 2C 1C 6G | 4G | 2G | 1C 5G 3G | 2C | 1C | 2C | | 4C | 1C 4G 2G |
|  |  |  |  |  | Post | 2.0 | 3C 6G 6Y | 3C 4H 8G | 3G | 3G 5U 9G | 5H 2H 8G 2C | 0 1C 8G | 0 | 2G 9C | 0 | 3G | 7G | | 3C | |
| CH3 | H | H | Cl | H | Pre | 0.4 | | 3C | 0 9U | 2C | 2C 5H | 5G | 0 | 9H | 9H | 0 | 1C | 8G | 9G | 0 |
|  |  |  |  |  | Post | 0.4 | 8C 8G 6Y | 9G | 9G | 9U 2H 9G | 6C 8H | 8G | 8G | &C | 1C 5G 2C 1C 9H | 4G | 9G 9C | 8G &C | 9C | 1C 9G |
| F | Cl | H | H | H | Pre | 0.4 | | | | | | | | | | | | | | |
|  |  |  |  |  | Post | 0.4 | 9C | 6C 9G | 2C 9H 8G 2H 9G | 2C 9G 3U 9G | 2C 9G 9C 5H 6C 8H | 2G 5G 6G | 1C 7G 5G 2G | &E 2C 9H 9C | &E 1C 5G 2C 1C 9H | 4G 1C | 1C 9G 9C | 2C 8G 7G 6F 9G | 9C 2C 8G 9G | 0 9G |
| CH3 | H | H | H | H | Pre | 0.4 | 9C 5C 6Y | 9C 5C 7G | 2C 2C 9G 4H 9G | 2H 2C 9G 7G | 9C 2G 9C 1C 3H 4H 9G | 2G 0 | 2G 0 | 2G 9C | 9H 9G | 2G 2G | 9C 9C 4C 8G | 9H 9G 7G | 5C 6G 2G | 5G 5G 0 |
| C2H5O | H | H | C2H5OH | H | Pre | 0.4 | 5C 6Y | 5C 7G | 2C 9G 4H 9G | 2H 7G 7H | 1C 3H 4H 9G | 2G | 0 | 9H | 9G | 2G | 3G | 8G | 3G | 0 |
|  |  |  |  |  | Post | 0.4 | 3C 9G 6Y | 5C 8G | 2C 8H 6H | 2H 7G 7H | 1C 3H 4H 9G | 2G | 0 | 9H | 9G | 2G | 3G | 8G | 3G | 2C 6G |
| CH3 | Cl | H | Cl | H | Pre | 0.4 | | | 1H | 5G | 5H | 3G | 0 | 9H | 1C 7H 1C | 1C | 4C 9G | 5C 9G | 3C 7G | 0 |
|  |  |  |  |  | Post | 0.4 | | 1C | 8G | 2G | 2C 5H | 2G | 0 | 7G | 2G 9H | 1H | 9G | 7G | 5C 3C 8G | 5G |
| CH3 | H | H | CH3 | H | Pre | 0.4 | 2C 9G 6Y | 1C 3H 7G | 2G 9G | 2G 8G | 1G 1H | 0 7G | 2G 6G | 2G 8H | 2G 9H | 2G 4G | 8G 6G | 2C 9G | 5C 3C 8G | 5G 0 |
|  |  |  |  |  | Post | 0.4 | 8G 6F 7F | 0 | 2G 9G | 3G | | 6G | 5G | 0 | 4G | 3G | 5G | 3H 1H | 5G 2G | |
| CH3 | H | H | NO2 | H | Pre | 0.4 | | | 3G | | | | | | | | | 0 | 0 | 0 |

Table VI—continued

| R3 | R4 | R5 | R6 | R7 | Mode of Application | Rate Kg/Ha | BUSH BEAN | COTTON | SOR-GHUM | CORN | SOY-BEAN | WHEAT | WILD OATS | RICE | BARN-YARD-GRASS | CRAB GRASS | MORN-ING-GLORY | COCK-LEBUR | CASSIA | NUT-SEDGE |
|---|---|---|---|---|---|---|---|---|---|---|---|---|---|---|---|---|---|---|---|---|
| Cl | H | H | CH3 | H | Pre | 0.4 | 7C | 2H | 6U | 9H | 3C | 1G | 3G | 2C | 9H | 2G | &C | 9C | 3C | 9G |
|  |  |  |  |  | Post | 0.4 | 9G | 4C | 9G |  | 9G |  |  | 8G |  |  |  |  | 8G |  |
|  |  |  |  |  | Post | 0.4 |  | 8G |  |  |  |  |  |  |  |  |  |  |  |  |
| Br | H | H | Br | H | Pre | 0.4 | 1C | 3H | 2C | 2C | 8H | 2G | 4G | 9H | 7G | 2G | 9G | 2C | &E | &E |
|  |  |  |  |  | Post | 0.4 | 9G | 3C | 7G | 8G | 2C |  |  |  | 7G |  |  | 7G | &E |  |
|  |  |  |  |  | Post | 0.4 | 6Y | 9G | 6G | 5G | 8G |  |  |  |  |  |  | 9G |  |  |
| CH3OH | H | H | Cl | H | Pre | 0.4 |  |  | 3G | 4G | 0 | 4G | 2G | 7G | 3C | 3C | 1C | 5H | 5H | 2C | 0 |
|  |  |  |  |  | Post | 0.4 | 1C | 2H | 9H | 7H | 2H | 4G | 0 | 8G | 9H |  | 7G |  |  | 5G |  |
|  |  |  |  |  | Post | 0.4 | 9G | 3C |  |  | 9G |  |  |  |  |  |  |  |  | 3G |  |
|  |  |  |  |  |  |  | 6Y | 8G |  |  |  |  |  |  |  |  |  |  |  | 6G |  |
| CH3OH | H | H | CH3O | H | Pre | 0.4 |  |  |  |  | 0 | 0 | 0 | 5G | UP | 5G | 0 | 5G | 0 | 2C | 3G |
|  |  |  |  |  | Post | 0.4 | 5C | 2C | 1C | 1C | 2H | 2G | 5G | 8G | 8H | 4G | 9C | 9H |  | 2C | 4C |
|  |  |  |  |  | Post | 0.4 | 9G | 2H | 6U | 4G | 7G |  |  |  |  |  |  |  |  | 7G | 8G |
|  |  |  |  |  |  |  |  | 8G | 2U |  |  |  |  |  |  |  |  |  |  |  |  |
|  |  |  |  |  |  |  |  |  | 8G | 8G |  |  |  |  |  |  |  |  |  |  |  |
| CH3 | CH3 | H | CH3 | CH3 | Pre | 0.4 |  |  | 1C | 7G | 1C | 3G | 6G | 4G | 5G | 4G | &E | 2C | 1C | 0 |
|  |  |  |  |  | Post | 0.4 | 3C | 3C | 8G | 2G | 8G | 1C | 1C |  | 2C | 1C |  | 2C | 7G | 1C | 6G |
|  |  |  |  |  | Post | 0.4 | 9G |  | 6G |  |  |  |  |  |  |  | 7H |  | 5G |  |
|  |  |  |  |  |  |  | 6Y |  |  |  |  |  |  |  |  |  |  |  |  |  |
| CH3 | H | H | (CH3)2CH | H | Pre | 0.4 |  |  | 8G | 1C | 3H | 3G | 5G | 1C | 2C | 2G | 5G | 0 | 5G | 9G |
|  |  |  |  |  | Post | 0.4 | 2S | 1H |  | 5G | 2H | 0 | 0 | 9H | 0 | 0 | 5G | 1H | 0 | 0 |
|  |  |  |  |  | Post | 0.4 | 6G | 2C |  | 6H | 5G |  |  | 2H |  |  |  |  |  |  |
|  |  |  |  |  |  |  | 6Y |  |  |  |  |  |  |  |  |  |  |  |  |  |
| CF3 | H | H | H | H | Pre | 0.4 |  |  | 0 | 3G | 0 | 0 | 2G | 0 | 4G | 5G | 8G | 8G | 0 | 0 |
|  |  |  |  |  | Post | 0.4 | &C | 9C | &C | 9C | 9C | 9C | 8G | 8G | 9C | 9G | &C | &C | 9G | 9C |
|  |  |  |  |  | Post | 0.4 |  |  | 9H |  | 5G |  | 6C |  | 3C | 5C |  |  | 6C |  |
|  |  |  |  |  |  |  |  |  |  |  | 9H |  | 7G |  | &E | 9G |  |  | 8G |  |
| F | H | H | H | F | Pre | 0.4 |  |  |  |  |  |  |  |  |  |  |  | &E | 9G |  |
|  |  |  |  |  | Post | 0.4 | 9C | 3C | 4C | 4U | 4H | 5G | 2G | 2C | 2C | 2C | &C | 9C | 6C | 9C |
|  |  |  |  |  | Post | 0.4 |  | 8D | 9G | 8G | 9C | 9C |  | &E | 8G | 9H |  |  |  | 9G |
|  |  |  |  |  |  |  |  | 9G |  |  |  |  |  |  |  | 7C |  |  |  |  |
| Cl | H | H | H | Cl | Pre | 0.4 |  |  | 2C | 1C | 9H | 9C | 8G | &E | 2C | 1C | 8G | 8G | 9G | 7G |
|  |  |  |  |  | Post | 0.4 | 9C | 9C | 9H | 8G | 0 | 2G | 4C | 8G | 9H | 7G | &C | &C | 9C | 7C |
|  |  |  |  |  | Post | 0.4 |  |  | &C | 9C |  |  | 9G | 4C | 9C | 9C |  |  |  |  |
| CH3OH | H | CH3O | H | H | Pre | 0.4 |  |  | &E | &E | 9H | 9H | 8G | 9G | 8G | 9H | 9G | 8G | &E | &E |
|  |  |  |  |  | Post | 0.4 | 1C | 0 | 8H | 3G | 0 | 2G | 4C | 0 | 1C | 3C | 2C | 0 | 0 | 2C |
|  |  |  |  |  | Post | 0.4 | 6Y | 3C |  |  |  |  | 9G |  | 8G | 6G |  |  |  | 1C |
|  |  |  |  |  |  |  |  |  |  |  |  |  |  |  | &E | 2C |  |  |  | 5G |
|  |  |  |  |  |  |  |  |  | 9H | 2C |  | 4G | 5G | &E | 2C | 4G | 8G | &E | 2C | 8G |

Table VI—continued

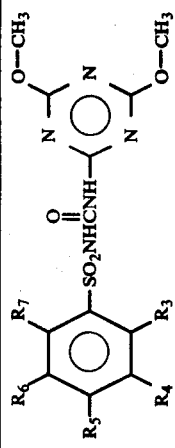

| R3 | R4 | R5 | R6 | R7 | Mode of Application | Rate Kg/Ha | BUSH BEAN | COTTON | SOR-GHUM | CORN | SOY-BEAN | WHEAT | WILD OATS | RICE | BARN-YARD-GRASS | CRAB GRASS | MORN-ING GLORY | COCK-LEBUR | CASSIA | NUT-SEDGE |
|---|---|---|---|---|---|---|---|---|---|---|---|---|---|---|---|---|---|---|---|---|
| Cl | CH3 | H | H | H | Post | 0.4 | 9C | 9C | 9U 9G 9H | 5C 9G 9H | 5C 9G 9H | 1C 4G 8G | 1C 3G 1C | 9C | 9C | 1H 5G 1C | 9C | &C | 9C | 4C 9G 7G |
| | | | | | Post | 0.4 | | | | | | | | &E | 9H | | 9G | 9G | 4C 9G | |
| | | | | | Pre | 0.4 | | | | | | | | | | | | | | 5C 8G | |
| | | | | | Pre | 0.4 | | 2C 2H 9G | 2H 8G | 9H | 6C 9G | 0 | 0 | 8G | 2C 8H | 5G 1C 5G 4G | 2C 9G | 2C 9G | | 7G |
| CH3 | H | H | H | H | Post | 0.4 | 2H 9D 9G | | 8G | 9G | 8H | 2G | 2G | &E | 2C 8G 5C 9G | 5G | 9G | 9G | 9G | 7G |
| | | | | | Post | 0.4 | | | | | | | | | | | | | | | |
| | | | | | Pre | 0.4 | | | | | | | | | | | | | | | |
| CH3 | H | H | CH3 | H | Post | 0.4 | 5C 9G 6F | 9C | 5U 9G | 3C 9G | 5C 9G | 1C | 1C 5G | 5C 9G | 2C 8G 5C 9G | 7G | &C | 9C | 9C | 3C 8G |
| | | | | | Post | 0.4 | | | | | | | | | | | | | | | |
| | | | | | Pre | 0.4 | | | 9G | 1C 9G | 9H | 7G | 7G | &E | 9H | 2G | 9G | 9G | 9G | 8G |
| | | | | | Pre | 0.4 | | | | | | | | | | | | | | | |

Table VI—continued

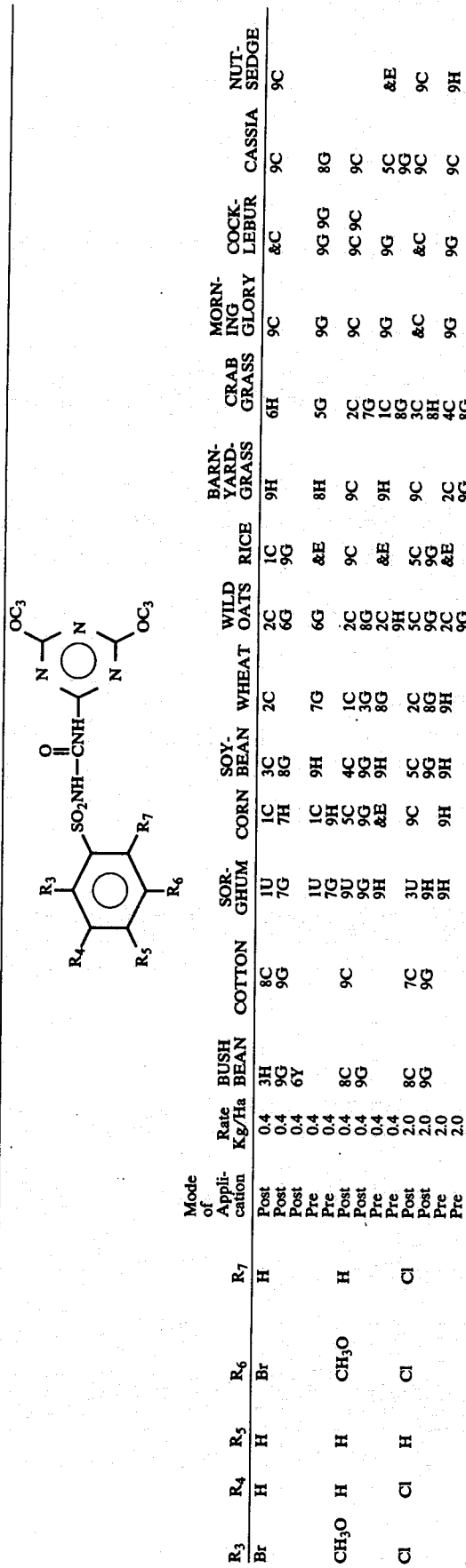

| R$_3$ | R$_4$ | R$_5$ | R$_6$ | R$_7$ | Mode of Application | Rate Kg/Ha | BUSH BEAN | COTTON | SOR-GHUM | CORN | SOY-BEAN | WHEAT | WILD OATS | RICE | BARN-YARD-GRASS | CRAB GRASS | MORN-ING GLORY | COCK-LEBUR | CASSIA | NUT-SEDGE |
|---|---|---|---|---|---|---|---|---|---|---|---|---|---|---|---|---|---|---|---|---|
| Br | H | H | Br | H | Post | 0.4 | 3H | 8C | 1U | 1C | 3C | 2C | 2C | 1C | 9H | 6H | 9C | &C | 9C | 9C |
|  |  |  |  |  | Post | 0.4 | 9G | 9G | 7G | 7H | 8G | | 6G | 9G | 8H | | | | | |
|  |  |  |  |  | Pre | 0.4 | 6Y | | | | | | | | | | | | | |
| CH$_3$O | H | H | CH$_3$O | H | Pre | 0.4 | | | | | | | | | | | | | | |
|  |  |  |  |  | Post | 0.4 | 8C | 9C | 1U | 1C | 9H | 7G | 6G | 9C | 8H | 5G | 9G | 9G 9C | 8G | |
|  |  |  |  |  | Post | 0.4 | 9G | | 7G | 9H | | | | | | | | | | |
|  |  |  |  |  | Pre | 0.4 | | | 9U | 5G | 4C | 1C | 2C | &E | 9C | 2C | 9C 9C | 9C | &E |
|  |  |  |  |  | Pre | 0.4 | | | 9G | 9G | 9G | 3G | 8G | | | 7G | | | | |
|  |  |  |  |  |  |  | | | 9H | &E | 9H | 8G | 2C | 5C | 9H | 1C | 9G | 9C | 5C | |
| Cl | Cl | H | Cl | Cl | Post | 2.0 | 8C | 7C | 3U | 9C | 5C | 2C | 5C | 5C | 9C | 8G | &C | &C | 5G | &E |
|  |  |  |  |  | Post | 2.0 | 9G | 9G | 9H | 9H | 9G | 8G | 9G | 9G | | 3C | | | 9C | 9C |
|  |  |  |  |  | Pre | 2.0 | | | 9H | | 9H | 9H | 2C | &E | 2C | 8H | | | 9C | |
|  |  |  |  |  | Pre | 2.0 | | | | | | | 9G | 9G | 9G | 4C 8G | 9G | 9G | 9C | 9H |

Table VI—continued

| R3 | R4 | R5 | R6 | R7 | Mode of Application | Rate Kg/Ha | BUSH BEAN | COTTON | SOR- GHUM | CORN | SOY- BEAN | WHEAT | WILD OATS | RICE | BARN- YARD- GRASS | CRAB GRASS | MORN- ING- GLORY | COCK- LEBUR | CASSIA | NUT- SEDGE |
|---|---|---|---|---|---|---|---|---|---|---|---|---|---|---|---|---|---|---|---|---|
| H | H | H | H | H | Post | 2.0 | 1S 6G 6Y | 3C 9G | 7G 5L | 2U 9G | 3C 9G | 3G 5X | 5G | 3C 8G | 2C 9H | 2C 5G | 9C | 4C 8G | 7C | 5C 5G |
| | | | | | Post | 2.0 | | | 7G | 9G | 9G | 5G | 5G | &E | 2C 8G | 8G | 8G | 8G | 7G | &E |
| Cl | H | Cl | H | Cl | Post | 2.0 | 3C 9G 6Y | 6C 9G | 7H | 7H | 3H 7G | 0 | 0 | 0 | 3H | 0 | 5C 8G | 6C 9G | 6C | 8G |
| Cl | H | H | H | H | Pre | 0.4 | 9C | 9G | 8H | 8G | 2H | 5G | 7C 2G 6G | 6G | 5G | 4G | 8G | 9G | 1C | 2C 9C 7G |
| | | | | | Post | 0.4 | | | 3C 1C 8G 6G | 9C 1C 9G 1U 3H | 7G 9G | 7C 7G 3G | 2G | 9C &E | &C 2C | 5C 2G 6G 2G | 9C 9G | &C 9G | &C 9G | 1C 5G |
| Cl | Cl | H | H | H | Pre | 0.4 | 4C 6Y 8G | 5C 6G 9G | 1H 5G 8G | 9G | 9H | 3G | 2G | &E | 2H 6G | 2G | 9G | 2H 8G &P 8H | 9G | &E |
| CH3 | CH3 | H | CH3 | CH3 | Post | 0.4 | 6C 9G | 5C 9G | 1C 6H 2C 8G | 1C 6H 2C 9G | 3H 9G 9H | 1G | 2G | 1C 7G &E | 1H 3G 7H | 5C 8G | 9C | 5C 8G &B | 6C 9G 3G | 5G |
| H | Cl | H | Cl | H | Pre | 0.4 | 1C 4H | | 1C 5G | 6G | 2C 2H | 0 | 4G | 1C 7G | 7H | 5G | 2C 4G | 7G | 5C | 9G |
| F | H | H | F | H | Post | 0.4 | 2C 5H 8G | 3C 4H 8G | 4G | 8G | 1C 7G 7H | 2G | 6G | 1C 7G | 2G | 0 | 8G | 9G | 2C 7G | 0 |
| F | H | H | H | H | Pre | 2.0 | | 2C 9G | 3C 9H 9H | 9H | 5C 8G 9H | 2C | 3G | 9C | 9H | 2C 5G 1C 6G | 8C | 9C | 8C | 2C 8G 1C 9G |
| | | | | | Post | 0.4 | | 5C 8G | 8U 9G 2H | 9G | 5H 9G 8H | 9G | 6G | &E | 2C 9H &C | 5G | 9G | 9G | 9C | 8G 9G 9G |
| F | H | H | H | F | Post | 0.4 | 9C | 9C | 8U 9G &C | &C | 5C 9G 9H | 5G | 3C | 9C | 9H | 1C 6G 8C | 4C 7G 9G | 7G | 3C 7G 8C | 1C 9G 1C 8G |
| Cl | H | H | H | Cl | Post | 0.4 | 9C | 9C | 2U 9G | 8H | 5H 9G 9H | 9H | 1C 4G 2G 9H | &E | 9H | 2C 9C 5C 1C 4G | 9G | 9G | 9C | 1C 8G 9C |
| H | Cl | H | H | H | Pre | 0.4 | 9C | 9C | 4U 9G | &C | 5H 9G | 5G | 3C | 9C | &C | 2C 5C | 9C | &C | 9C | &E |
| H | Cl | H | H | H | Pre | 0.4 | 9C | 9G | 1U 9G | 9G | 9G | 1H 7G 3C | 1C 6G 2G | &E | 9H | 2C 1C 4G | &C | 9C | 9G | 8G |
| H | Cl | H | H | H | Post | 0.4 | 9C | 5C | 5U | 8U | 9C | 3C | | 9C | 6C | 4G | &C | &C | 9C | 1C |

Table VI—continued

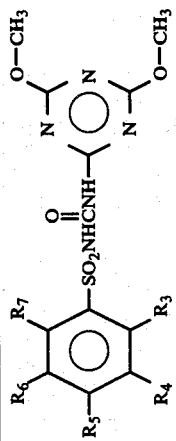

| R3 | R4 | R5 | R6 | R7 | Mode of Application | Rate Kg/Ha | BUSH BEAN | COTTON | SOR-GHUM | CORN | SOY-BEAN | WHEAT | WILD OATS | RICE | BARN-YARD-GRASS | CRAB GRASS | MORN-ING-GLORY | COCK-LEBUR | CASSIA | NUT-SEDGE |
|---|---|---|---|---|---|---|---|---|---|---|---|---|---|---|---|---|---|---|---|---|
| F | H | H | CH3 | H | Post | 0.4 | 2C 7G 6F | 9G | 9G 9H | 9G &E | 9H | 8G | 1C 6G | &E | 9H 2C 3H | 5G | 9G | 9G | 5C 5C 8G | 5G 1C 7G 2C 8G |
| Cl | H | H | H | CH3 | Pre | 0.4 | 9C | 2H 5C 9G | 6G | 4G | 5C 9G | 0 | 0 | 4C 6G 9H | 2G | 2G | 5C 9G | 9C | 9G | 9C |
| CH3O | Cl | H | H | H | Post | 0.4 | 2H 9D 9G | 5C 9G | 8G | 2C 8G 9G | 4C 8G 9H | 5U 8G &E | 3C 8G 2C 8G | 3C 8G &E | 9C 9H | 5G 9H | 5G 9C | 9G 9C | 9C | 3C 8G 2C 8G | 8C &E 2C 8G |
| CH3 | H | CH3 | H | CH3 | Pre | 0.4 | 1C 9G 6F | 7C 9G | 5U 9G | 2C 9H | 4C 9G | 0 | 0 | 9G | 9H | 0 | 9C | 9G | 9G 9C | 3C 9G | 7G 2C 8G |
| NO2 | H | H | H | H | Post | 0.4 2.0 | 9C 9C | 3C 2H 8G 9C | 8H 3H 8G 3G 2U 8G 3C 9G &E | 9G 2C 9H 7H 1C 6G 9C 7U 9G &E | 9H 3H 9G | 3C 7G 4G | 3C 8G 4G 0 | 3C 8G &E 8C | 9C 0 0 | 4G 1C 0 8C 9C | 9G 9C &C &C | 9G 9C &C &C | 9G 9C 5C &E | 9G 3C 9G | 7G 2C 8G 9G &C &E |
| C2H5O | H | H | C2H5O | H | Pre | 2.0 | 6C 9G | 8C 9G | 9G | 1C 9G 1C 9G | 9H 3H 8G | 2H 8G 1C 3G 7G | 2C 8G 1C 6G | &E 7G | 9H 3C 9H | 9G 2C | 9G 9C | 9G 9C | 9G 5C 9G &E | 9G 9C | 9G &E |
| CH3O | H | H | F | H | Post | 0.4 | 9C | 9C | 3U 9H | 6U &E | 3H 9H | 4C 9H | 1C 2C 9G | 3C &E | 6C 9H | 9H | 9G | 9C | 5C 9G 9C | 6C 9G | 6C &E |
| C2H5O | H | H | Cl | H | Post | 0.4 | 9C | | 2U 9H | 9H 9G | 3H 8G 9H | 5G 6G | 9G 9C 1C 7G | 4C &E | 6C 9H | 1C 9G | &C 9G | 9G 9C | 9G 9C | 6C 9G | 2C 9G |
| Cl | H | H | CH3 | H | Post | 0.4 | 4C 9G 6Y | 9C | 5U 9G | 8H | 4H 9G | 2G | 6G 8G | 3C 8G | 2C 9H | 2C 8G | &C | 9C &E | 9C | 6C 9G | 2C 8G |
| CH3 | H | H | NO2 | H | Post | 0.4 | 6S 9G 6Y | 2H 4C 9G | 3U 9G | 9H 4C 9G | 4C 9G | 6G 8G | 6G 8G | 3C 9G | 9H 5C 9H | 3C 7G 2C 8G | 3C 7G 2C 8G | &C 5G | 8H | 9G 3C 7G | &E 9G |

Table VI—continued

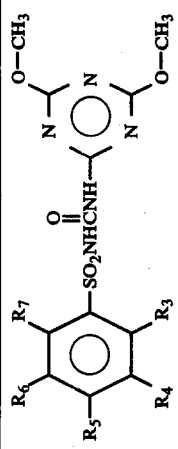

| R3 | R4 | R5 | R6 | R7 | Mode of Application | Rate Kg/Ha | BUSH BEAN | COTTON | SOR-GHUM | CORN | SOY-BEAN | WHEAT | WILD OATS | RICE | BARN-YARD-GRASS | CRAB GRASS | MORN-ING-GLORY | COCK-LEBUR | CASSIA | NUT-SEDGE |
|---|---|---|---|---|---|---|---|---|---|---|---|---|---|---|---|---|---|---|---|---|
| F | H | H | H | H | Pre | 0.4 | | | 3C | 9G | 7H | 9H | 8G | 9H | 9H | 8G | 6G | | 0 | 9G |
| | | | | | Pre | 0.4 | 6C | 6C | 9G | 5C | 6C | 0 | 0 | 3C | 5C | 2C | 9C | 9C | 9C | 1C |
| | | | | | Post | 0.4 | 9G | 9G | 9G | 9G | 9H | 2G | 2G | 8G | 9H | 6G | 9C | 9C | 9C | 8G |
| | | | | | Post | 0.4 | | | 8G | 9G | 9H | 2G | 3G | 9H | 9H | 1C | 9C | 9C | 9C | &E |
| CH3O | H | H | CH3 | H | Pre | 0.4 | 5C | 9C | 3C | 3G | 7C | 2G | 3G | 7C | 3C | 7G | &C | 3C | 5C | 0 |
| | | | | | Post | 0.4 | 3G | | 5G | 8G | 5G | | | 4G | | 0 | | | | |
| | | | | | Pre | 0.4 | 6Y | | | | | | | | | | | | | |
| CH3 | H | H | (CH3)2CH | H | Pre | 0.4 | 4H | 5C | 4C | 8G | 7C | 2C | 3G | 7G | 5C | 2G | 7G | 4G | 5G | 3G |
| | | | | | Post | 0.4 | 9G | 8G | 5G | 9H | 5G | 1C | 1C | 3C | 1C | 1C | &C | 5C | 2C | 0 |
| | | | | | Post | 0.4 | 6Y | | 2C | | 3C | 4G | | 9G | 4G | 5G | | 9G | | |
| | | | | | Pre | 0.4 | | | 9H | | 9C | | | | | | | | | |
| CF3 | H | H | H | H | Pre | 0.4 | 9C | 9C | 2C | 1C | 5H | 8G | 7G | 9H | 2C | 4G | 9G | 8G | 5G | &E |
| | | | | | Post | 0.4 | | | 9G | 9G | 9G | 3G | 3G | 5G | 9C | 5G | &C | 8C | 9C | 9C |
| | | | | | Post | 0.4 | | | 7G | 8G | 5C | 3G | 3G | 2C | 7G | 2C | 9G | | 6G | 7G |
| | | | | | Pre | 0.4 | | | 5G | 8G | | | | 8H | | 0 | | | 9G | 9C |
| F | H | H | H | F | Pre | 0.4 | 9D | 9C | 8G | 8G | 9G | 7G | 4G | 7G | 9G | 5G | 9C | 9G | 9C | &E |
| | | | | | Post | 0.4 | 9G | | 9H | 8G | 5C | 2C | 8G | 2C | 3C | 1C | 4G | &E | 5C | 7G |
| | | | | | Post | 0.4 | 6G | | 0 | 5U | 9H | 8G | 0 | &E | 9H | 0 | 9G | 4C | &C | &E |
| | | | | | | | | | | 2G | 2H | | | 4G | 1C | | | 7G | | |
| Cl | H | Cl | H | H | Pre | 0.4 | | | 0 | 1C | 5H | 0 | 0 | 6G | 1C | 3G | &E | 9G | 6C | 5G |
| | | | | | Post | 0.4 | 4S | 2C | 3C | 7G | 3C | 1C | 7G | 5C | 9C | 5C | 2C | 3C | 3C | 2C |
| | | | | | Post | 0.4 | 8G | 4H | 9G | 2C | 7G | 7G | | 7G | | 9G | 6H | 8H | | 7G |
| | | | | | Pre | 0.4 | 6Y | | | 8G | | | | | | | | | | |
| Cl | H | NO2 | H | H | Pre | 0.4 | 8D | 2C | 9G | 8G | 2C | 9G | 7G | &E | 9H | 3G | 3G | 9G | 7G | 5G |
| | | | | | Post | 0.4 | 9G | 3H | 2C | 9H | 9C | 6G | 8G | 5C | 1C | 5G | 9C | 9C | 9C | 9G |
| | | | | | Post | 0.4 | 6Y | 9G | | | | | | &E | | | | | | |
| CH3O | H | H | Cl | H | Pre | 0.4 | 4S | 2H | 9H | 9H | 9H | 8G | 8G | 8G | 9H | 4G | 3G | 9G | 9C | 4G |
| | | | | | Post | 0.4 | 7G | 5C | 5G | 3H | 3G | 0 | 0 | 3G | 2H | 1C | 2H | 2H | 2G | 0 |
| | | | | | Post | 0.4 | 6Y | 7G | | 7G | 7G | | | | 7H | | 4H | | | |
| | | | | | Pre | 0.4 | | | | 5X | | | | | | | | | | |
| F | F | F | H | F | Pre | 0.4 | 9C | 6C | 2H | 2C | 9H | 8G | 0 | &E | 2C | 5G | 2C | 0 | 5C | 2C |
| | | | | | Post | 0.4 | | 9G | 9H | | 9H | 5C | 9H | 5C | 7H | 3G | 6G | 5C | 7G | 8G |
| | | | | | | | | | | | | 9G | 9G | &E | 9H | | 5C | 9G | 90 | 5C |
| | | | | | | | | | | | | | | | | | 9G | | | 5 |
| CH3 | H | H | F | H | Pre | 0.4 | | 2H | 3U | 2C | 1C | 1C | 9G | 5C | 4C | 3C | 9C | &C | 9C | 9C |
| Cl | H | H | CH3O | H | Post | 0.4 | &D | | | | | | | | | | | | | |

Table VI–continued

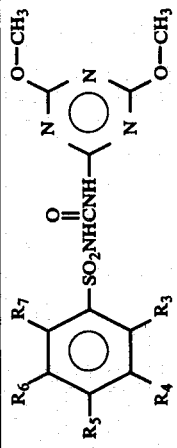

| R$_3$ | R$_4$ | R$_5$ | R$_6$ | R$_7$ | Mode of Application | Rate Kg/Ha | BUSH BEAN | COTTON | SOR-GHUM | CORN | SOY-BEAN | WHEAT | WILD OATS | RICE | BARN-YARD-GRASS | CRAB GRASS | MORN-ING-GLORY | COCK-LEBUR | CASSIA | NUT-SEDGE |
|---|---|---|---|---|---|---|---|---|---|---|---|---|---|---|---|---|---|---|---|---|
| Cl | H | H | CF$_3$ | H | Post | 0.4 | 9G | 5C<br>9G | 9G | 7G | 3H<br>9H | 0 | | 9G | 9H | 7G | 9G | 9G | 9C | &E |
| | | | | | Post | 0.4 | | | 1C<br>8H | 7G | 3H<br>9G | 0 | 8G | &E | 9H | 3C<br>6G | 9C | 9C | 3C<br>9G | 9G |
| | | | | | Pre | 0.4 | 4H<br>9G<br>6Y | 3C<br>3H<br>9G | 6G | 8H | | 6G | 0 | 9P<br>9G | 6G | 0 | | | | | 1C<br>8G |
| H | Cl | Cl | H | H | Post | 0.4 | 3H<br>8G<br>6Y | 2C<br>3H<br>8G | 8G | 7G | 8H | 6G | 5G | &E | 7H | 0 | 9G | 9G | 5C<br>9G | 0 |
| | | | | | Pre | 0.4 | | | 6G | 9H | 3H<br>9G | 0 | 0 | 8G | 2G | 0 | 1B<br>8G | 1B<br>8G | 2C<br>6G | 3G |
| Cl | Cl | Cl | H | H | Post | 2.0 | 5C<br>9H | 5C<br>9G | 1C<br>6G<br>3H | 1C<br>9G<br>4H | 2C | 6G | 2G | 9H | 1C<br>6G<br>1H | 0 | 9G | 9G | 5G | 1C<br>9G |
| | | | | | Pre | 2.0 | 4S<br>9G<br>6Y | 5C<br>9G | 1H<br>2G | 1C<br>3C | 2C<br>8H<br>5G | 0 | 0 | 5G | 1H<br>2C | 1C | 5C<br>9G | 9H | 5C<br>9G | 2C<br>9G |
| Cl | H | H | Cl | H | Post | 2.0 | | | 0 | 6G | 2C<br>7G | 5G | 0 | 9H | 3C | 2C | 9G | 7G | 5C | 0 |
| | | | | | Pre | 2.0 | 2C<br>6G<br>6Y | 7C<br>9G | 2C<br>8G | 9H | 2C<br>3H<br>9G | 4G | 4G | 6C<br>9G | 9H | 2H<br>5G | &C | &C | 9G<br>8G | 9C |
| Cl | H | H | Cl | H | Post | 0.4 | | | | 2U<br>9H | &G<br>9H | 8G | 7G | &E | 2C<br>9H | 1C<br>5G | 9G | &E | 3C<br>9G | 7G |
| | | | | | Pre | 0.4 | | | 9H | | | | | | | | | | | |

Table VI–continued

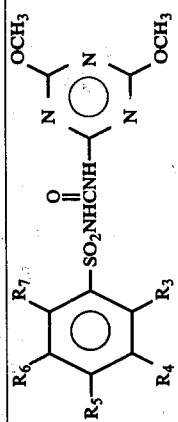

| R$_3$ | R$_4$ | R$_5$ | R$_6$ | R$_7$ | Mode of Application | Rate Kg/Ha | BUSH BEAN | COTTON | SORGHUM | CORN | SOYBEAN | WHEAT | WILD OATS | RICE | BARNYARD GRASS | CRABGRASS | MORNING GLORY | COCKLEBUR | CASSIA | NUTSEDGE |
|---|---|---|---|---|---|---|---|---|---|---|---|---|---|---|---|---|---|---|---|---|
| Cl | H | H | H | Cl | Post | 0.4 | 9C | 9C | 9G | 9C | 9C | 9C | 8C | 8G | 9C | 8C | &C | &C | 9C | 9C |
|  |  |  |  |  | Post | 0.4 |  |  | 6C |  |  |  |  | 5C |  |  |  |  |  |  |
|  |  |  |  |  | Pre | 0.4 |  |  | 9H | 9G | 9H | 9H | 1C | &E | 9H | 9G | 9G | &E | 9G | 9G |
|  |  |  |  |  |  |  |  |  |  |  |  |  | 8G |  |  |  |  |  |  |  |
|  |  |  |  |  |  |  |  |  |  |  |  |  | 4G |  |  |  |  |  |  |  |
| NO$_2$ | H | H | H | H | Post | 0.4 | 9C | 9C | 9G | 9G | 9C | 4G | 1C | 4C | 9C | 9C | &C | 9G | 9C | &C |
|  |  |  |  |  | Post | 0.4 |  |  | 3C | 7U |  |  | 6G | 8G |  |  |  | 5C |  |  |
|  |  |  |  |  | Pre | 0.4 |  |  | 9G | 1C |  |  | 4G | &E |  |  |  | 9G |  |  |
|  |  |  |  |  | Pre | 0.4 |  |  |  | 9G |  |  |  | 9C |  |  |  |  |  |  |
|  |  |  |  |  | Post | 0.4 | 3C | 6C | 7G | 9H | 9H | 2H | 1C | 2C | 9H | 9C | 9G | 9C | 3C | 1C |
|  |  |  |  |  | Post | 0.4 | 7G | 9G |  |  |  | 8G | 6G | 6G |  |  |  |  | 7G | 8G |
|  |  |  |  |  | Pre | 0.6 | 6Y |  |  |  |  | 0 | 0 |  |  |  |  |  |  |  |
| H | CH$_3$ | H | H | H | Pre | 0.4 |  |  | &E | 9G | 9H | 8G | 1C | &E | 2C | 2C | 9G | 8G | 9G | &E |
|  |  |  |  |  | Pre | 0.4 |  |  |  |  |  |  | 8G |  | 9H | 6G |  |  |  |  |

Table VI—continued

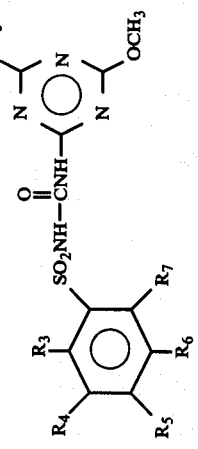

| R3 | R4 | R5 | R6 | R7 | Mode of Application | Rate Kg/Ha | BUSH BEAN | COT-TON | SOR-GHUM | CORN | SOY-BEAN | WHEAT | WILD OATS | RICE | BARN-YARD GRASS | CRAB-GRASS | MORN-ING GLORY | COCK-LEBUR | CAS-SIA | NUT-SEDGE |
|---|---|---|---|---|---|---|---|---|---|---|---|---|---|---|---|---|---|---|---|---|
| CH3 | H | H | H | H | Post | 0.4 | 9C | 9C | 9U | &C | 9C | 9C | 2C | 6C | &C | 8C | 9C | 9C | &C | 9C |
|  |  |  |  |  | Post | 0.4 |  |  | 9G | &E | 9H | 9G | 9G | 9G | 9H | 1C | &E | 9C | 9C | 9G |
| Cl | H | H | H | H | Pre | 0.4 |  |  | 1C | &C | 2C | 3C | 1C | 4C | 9C | 9C | 9C | &C | 9C | 9C |
|  |  |  |  |  | Pre | 0.4 | 9C | 9C | 9G | &C | 4H | 7G | 9G | 9G | &C | 9C | 9C | 9G | 9G | 9G |
|  |  |  |  |  | Pre* | 0.4 |  |  | 8U | &E | 9H | 9G | 1C | &E | 9H | 2C | 9C | &C | 9G | 9G |
|  |  |  |  |  | Post | 0.4 |  | 9C | 2C | 9G | 9H | 7G | 6C | &E | 2C | 8G | 9G | 9G | &E | 2G |
|  |  |  |  |  | Post | 0.4 |  |  | 9G | 9G |  |  | 1C | 8G | 9G | 9G | &C | 9G |  | 9G |
|  |  |  |  |  | Post* | 0.4 |  |  | 9H |  |  |  | 3C |  |  |  |  |  |  |  |
| F | Cl | H | H | H | Pre | 0.4 | 4C | 6C | 9U | &C | 5H | 5C | 1C | 6C | &C | 2C | 9C | 6C | 9C | 4G |
|  |  |  |  |  | Post | 0.4 | 9G | 9G | 9G | &E | 9G | 8G | 5C | 9G | 9H | 5G | 9C | 9G | 9G | 6G |
|  |  |  |  |  | Pre* | 0.4 | 6Y |  |  |  |  |  | 2C |  |  |  |  |  |  |  |
| Cl | Cl | H | H | H | Pre | 0.4 | 9C | 9C | 9G | &C | 9H | 9H | 5C | &E | 9H | 5G | 9C | &C | 9C | 5C |
|  |  |  |  |  | Post | 0.4 |  |  | &C | &C | 6C | 5C | 5G | 9C | &C | 2C | 9C | 9C | 9G | 9G |
|  |  |  |  |  | Pre* | 0.4 |  |  | 9H | &E | 9H | &E | &E | &E | 2C | 8G | 9C | 9C | 8G | 6G |
| H | Cl | Cl | H | H | Pre | 0.4 | 5H | 2C | 8H | 9H | 3H | 1C | 1C | 1C | 2C | 1C | 2H | 9C | 1C | 0 |
|  |  |  |  |  | Post | 0.4 | 9G | 2H |  | 1C | 9G | 5G | 9G | 9G | 7G | 6G | 9C | 9C | 4G | 3G |
|  |  |  |  |  | Pre* | 0.4 | 6Y | 9G |  | 8G |  | 8G |  |  | 2C | 2G | 5C |  |  |  |
|  |  |  |  |  | Post* | 0.4 |  |  |  | 9H |  | &E |  | &E | 8H |  | 9G |  |  |  |
| F | H | Cl | CH3 | H | Pre | 0.4 | 9C | 9C | 7G | 1C | 3H | 5G | 2G | &E | 4G | 1C | 2H | &C | 1C | 2C |
|  |  |  |  |  | Post | 0.4 |  |  | 2C | 8G | 5C | 1C | 1C | 9C | 9C | 4G | 9G | 9C | 7G | 6G |
|  |  |  |  |  |  |  |  |  | 8G | 9H | 5G |  |  |  |  |  | 5C |  | 5G | 2G |
|  |  |  |  |  |  |  |  |  | 2H | 3U | 9G |  |  |  |  |  | 9G |  | 8G |  |
| Cl | H | H | CH3O | H | Pre | 0.4 | 6C | 6C | 7U | 1C | 2C | 0 | 0 | 5C | 9C | 2C | 9C | 9C | 9C | 8C |
|  |  |  |  |  | Post | 0.4 | 9G | 9G | 9G | 9G | 9G | 2G | 8G | 9G | 9H | 5G | 9C | 9C | 9G | &E |
|  |  |  |  |  |  |  |  |  | &E | 9H | 9H | 5G | 0 |  | 7H | 9H | 5C |  |  | 9G |
|  |  |  |  |  |  |  |  |  | 2G |  | 9G |  |  |  |  | 0 | 9H |  |  |  |
| Cl | Cl | H | CF3 | H | Pre | 0.4 | 3H | 3C | 1H | 9H | 8H | 1C | 2G | &E | 6G | 0 | 9C | 9G | 9C | 0 |
|  |  |  |  |  | Post | 0.4 | 8D | 3H | 1C | 9H | 5C | 0 | 0 | 7G | 1C | 0 | 5C | 9C | 2C | 7C |
|  |  |  |  |  |  | 0.4 | 9G | 9G | 8H |  | 9G |  |  |  | 5H |  | 9H |  | 3C |  |
| Cl | H | Cl | H | H | Pre | 2.0 | 5C | 4C | 5G | 1C | 7H | 0 | 5G | 6G | 2H | 0 | 9C | 9G | 5G | 0 |
|  |  |  |  |  | Post | 2.0 | 9G | 9G | 6H | 6G |  |  |  |  |  |  |  |  |  |  |
|  |  |  |  |  |  | 2.0 | 6Y |  |  | 9H |  |  |  |  |  |  |  |  |  |  |
| Cl | H | Cl | Cl | H | Pre | 2.0 | 5C | 5C | 1H | 9H | 5C | 0 | 0 | 6G | 1C | 0 | 4C | 9C | 5C | 2C |
|  |  |  |  |  | Post | 2.0 | 9G | 9G | 1C | 9H | 9G |  |  |  | 7H |  | 9G |  | 9G | 8G |
|  |  |  |  |  |  | 2.0 | 6Y |  | 8H |  |  |  |  |  |  |  |  |  |  |  |

Table VI—continued

[Structure: benzene ring with substituents R3, R4, R5, R6, R7 and SO2NH-C(=O)-NH-[triazine with CH3 and OCH3]]

| R3 | R4 | R5 | R6 | R7 | Mode of Application | Rate Kg/Ha | BUSH BEAN | COTTON | SORGHUM | CORN | SOYBEAN | WHEAT | WILD OATS | RICE | BARNYARD GRASS | CRABGRASS | MORNING GLORY | COCKLEBUR | CASSIA | NUTSEDGE |
|---|---|---|---|---|---|---|---|---|---|---|---|---|---|---|---|---|---|---|---|---|
| Cl | H | H | Cl | H | Pre | 2.0 | | | 3G | 1C | 9H | 3G | 0 | 8H | 1C | 2G | 9G | 9G | 5C | 0 |
| | | | | | Pre | 2.0 | | 8C | 3U | 8G | 3C | 7G | 5G | 9C | 9C | 2H | &C | 9C | 9C | 9C |
| | | | | | Post | 0.4 | 9C | 9G | 9G | 9C | 9G | 2H | 8G | &E | 9H | 6G | 9G | 9C | 9G | 1C |
| Cl | CH3 | H | H | H | Pre | 0.4 | | | 1C | | | 8C | 1C | | | 2C | | | | | 9G |
| | | | | | Post | 0.4 | 9C | 8C | 9G | &C | 6C | 9G | 4G | 6C | 9H | 8G | &C | 9G | 9C | 2C |
| | | | | | | 0.4 | | 9G | &C | 9H | 9G | 9H | 9H | 9G | &E | | 5G | | | 8G |
| CH3 | H | H | CH3 | H | Pre | 0.4 | | | 5U | 5C | 4C | 1C | 9G | 5C | 5C | 2C | 5C | 9G | 8C | 1C |
| | | | | | Post | 0.4 | 9C | 9C | 9G | 9G | 9G | 2H | 1C | 9G | 9G | 6G | 9G | 9G | 9C | 7G |
| | | | | | | 0.4 | | | 9H | | 9H | 8G | 9H | &E | 9H | 8G | | | | 5C |
| Br | H | H | Br | H | Pre | 0.4 | | | 3U | 2C | 5C | 2H | 1C | 4C | 4C | 7G | | &C | 9G | 8G |
| | | | | | Post | 0.4 | 9C | 9C | 9G | 9H | 9G | 8G | 9H | 9G | 9H | | 5G | | | |
| | | | | | | 0.4 | | | 9H | 9G | 9H | 4G | 5G | &E | | | 9G | | | |
| CH3O | H | H | CH3O | H | Pre | 0.4 | | | 9U | &C | 5C | 8G | 4C | 9C | 9C | 6G | &C | 9G | 8C | 9G |
| | | | | | Post | 0.4 | 9C | 9C | 9G | &E | 9G | 9H | 9G | &E | 9H | 2C | 9G | | | |
| | | | | | | 0.4 | | | 9H | | 9H | | 9C | | | 9G | | | | |
| Cl | Cl | H | Cl | Cl | Pre | 0.4 | | | 5U | &C | 5C | 9H | 8G | 5C | 5C | 7G | 5G | &C | 9C | 3C |
| | | | | | Post | 0.4 | 9C | 9C | 9G | 9G | 9G | | 1C | 9G | 9G | 3C | 9G | | | 9G |
| | | | | | | 0.4 | | | &H | | 9H | | 7G | &E | 9H | 9G | | | | |
| CH3O | H | H | Cl | H | Pre | 2.0 | | | 9G | 9G | 9C | 9G | 9H | 9C | &C | 7G | 9G | 9G | 9C | 8G |
| | | | | | Post | 2.0 | 9C | 9C | 9G | 9G | 9G | 9H | | &E | 9H | 9C | &C | 9G | 9C | |
| Cl | Cl | H | Cl | CH3 | Pre | 2.0 | | | 5U | 9U | 5C | 8G | 1C | 5C | 5C | 2C | 9G | | | 8G |
| | | | | | Post | 0.4 | 6C | 6C | 9G | 9G | 9G | &G | 7G | 8G | 9H | 6G | &C | 9G | 9C | &E |
| | | | | | | 0.4 | 9G | 9G | 9H | &G | 9H | | 8C | &E | | 7G | | | | |
| Cl | Cl | H | H | H | Pre | 0.4 | | 2C | 2C | 9G | 9H | 8C | 2G | 2C | 9H | 9C | 9G | 9G | 8C | 2G |
| F | H | F | H | F | Post | 0.4 | 2C | 4H | 8G | | 3H | &E | 8G | 0 | 9H | 2C | 2G | 5C | 0 | &E |
| | | | | | Pre | 0.4 | 9G | 8G | | | 8G | 2G | 0 | 9H | 3C | 5G | 7G | 9G | 0 | 2G |
| Cl | H | Cl | H | Cl | Post | 0.4 | 6Y | | | | | 6G | | 0 | 8H | | 2G | | | |
| | | | | | Pre | 0.4 | 3C | 3C | 2C | 2C | 1C | 6G | 0 | 0 | 3C | 5G | 5C | 6C | 0 | 9G |
| | | | | | Post | 0.4 | 9G | 9G | 8G | 8H | 2H | | 0 | 0 | 8G | 2G | 9G | 9G | 4G | 8G |
| F | H | F | H | Cl | Pre | 0.4 | 6Y | | | | 8G | | | | 2H | | 7G | | | |
| CH3 | H | CH3 | H | CH3 | Post | 0.4 | 2C | 5C | 7H | 7G | 3H | 5G | 0 | 0 | 5G | 4G | 5C | 9G | 0 | 9G |
| | | | | | | 0.4 | | | 3H | 4G | 2H | 0 | 0 | 1C | 0 | 0 | 9G | 5C | 6G | &E 5C |

Table VI—continued

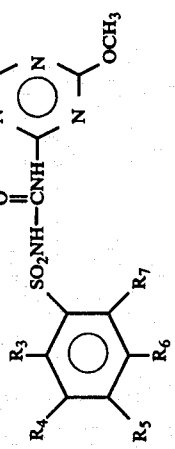

| R$_3$ | R$_4$ | R$_5$ | R$_6$ | R$_7$ | Mode of Application | Rate Kg/Ha | BUSH BEAN | COT-TON | SOR-GHUM | CORN | SOY-BEAN | WHEAT | WILD OATS | RICE | BARN-YARD GRASS | CRAB-GRASS | MORN-ING GLORY | COCK-LEBUR | CAS-SIA | NUT-SEDGE |
|---|---|---|---|---|---|---|---|---|---|---|---|---|---|---|---|---|---|---|---|---|
| CF$_3$ | | | | | Post | 0.4 | 9G | 9G | 9G | | 9G | 5G | 5G | 9G | 0 | | 9G | | 9G | 9G |
| | | | | | Post | 0.4 | 6F | | 1C | 1C | 9H | 6G | 6G | 9H | | 3G | 9G | 9G | 9G | 9G |
| | | | | | Pre | 0.4 | | | 8G | 8C | | 1C | 1C | | | | | | | |
| | H | H | H | H | Post | 0.4 | 9C | 9C | 9G | | 9C | 1C | 1C | 9C | 9C | 9C | &C | 9C | 9G | &C |
| | | | | | Post | 0.4 | | | 5U | | | 6G | 7G | 5C | 2C | 4C | | | 6G | |
| | | | | | Pre | 0.4 | | | 9H | | | 8G | | &E | 9C | 9G | 9G | &E | 9G | 7G |
| Cl | H | H | H | Cl | Post | 0.4 | 9C | 9C | 9C | 2C | 9H | 8G | 8C | 8G | 9H | 9C | 9C | 9C | 9C | 9C |
| | | | | | Post | 0.4 | | | | 9G | | 5C | | 5C | | | | | | | |
| | | | | | Pre | 0.4 | | | &E | &C | 9H | 9H | | &E | | | | | | | |
| NO$_2$ | H | H | H | H | Post | 0.4 | 8C | 9C | 9C | 9C | 9C | 9C | 2C | 8C | 9C | 9C | &C | &C | 9C | 9C |
| | | | | | Post | 2.0 | 9C | 9C | &C | 9C | 9C | 9C | 8C | 9C | 9H | 9C | 9C | &E | &E | &C |
| | | | | | Pre | 0.4 | | | &E | 2C | 9H | 9H | 7C | &E | &E | 9G | 9G | &E | 9G | 9G |
| | | | | | Pre | 2.0 | | | &E | &E | 9H | 9H | 8G | &E | &E | &E | 9G | 9G | &E | &E |
| | | | | | Pre | 0.4 | | | | 9G | | | 2C | 7G | | | | | | | |

*Duplicated Data

Table VI—continued

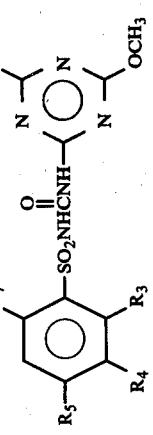

| R3 | R4 | R5 | R7 | X | Mode of Application | Rate Kg/Ha | BUSH BEAN | COT-TON | SOR-GHUM | CORN | SOY-BEAN | WHEAT | WILD OATS | RICE | BARN-YARD GRASS | CRAB-GRASS | MORN-ING GLORY | COCK-LEBUR | CAS-SIA | NUT-SEDGE |
|---|---|---|---|---|---|---|---|---|---|---|---|---|---|---|---|---|---|---|---|---|
| Cl | H | H | H | C₂H₅O— | Post | 0.4 | 2H 9D 9G | 2C 3H 9G | 9H | 2C 9H | 5C 9G | 1G | 1G | 5C 9G | 9H | 6G | 9C | 4C 9G | 5C 9G | 2C 7G |
|  |  |  |  |  | Post | 0.4 |  |  |  |  |  |  |  |  |  |  |  |  |  |  |
|  |  |  |  |  | Post | 0.4 |  |  |  |  |  |  |  |  |  |  |  |  |  |  |
|  |  |  |  |  | Pre | 0.4 |  |  |  |  |  |  |  |  |  |  |  |  |  |  |
|  |  |  |  |  | Pre | 0.4 |  |  |  |  |  |  |  |  |  |  |  |  |  |  |
| H | H | H | H | CH₃S— | Post | 2.0 | 1H | 3H 8G | 6G | 9H | 9H | 5G | 5G | &E | 2C 9G 1C | 2C | 9G | 3C 9G 5H | 2C 3H 9G 1C 5G 9G | 9G |
|  |  |  |  |  | Post | 2.0 |  |  |  |  |  |  |  |  |  |  |  |  |  |  |
|  |  |  |  |  | Pre | 2.0 |  |  | 0 | 2C | 2H 8G | 0 | 0 | 2G | 4G 6G | 1C | 5H | 0 | 0 |
| CH₃ | H | H | H | CH₃S— | Post | 2.0 | 5C 9G | 4C 9G | 7G 3G | 6G 5G | 8H 5C 9G 9H | 0 | 0 | 9H 5G | 4G 6G | 0 5G | 9G 5C 9G 9G | 9G 0 | 9G 1C 5G 9G | 5G 0 |
|  |  |  |  |  | Post | 2.0 |  |  |  |  |  |  |  |  |  |  |  |  |  |  |
|  |  |  |  |  | Pre | 2.0 |  |  |  |  |  |  |  |  |  |  |  |  |  |  |
| H | H | H | H | n-C₃H₇O— | Post | 2.0 | 3C 9G 6Y | 5C 9G | 2H 7G 2C 8H | 1C 9G 1C 9G | 2C 8G 8H | 3G | 2G | 2C 7G | 3C 8G | 2C 5G | 2C 8G | 1H 7G | 3C | 7G |
|  |  |  |  |  | Post | 2.0 |  |  |  |  |  |  |  |  |  |  |  |  |  |  |
|  |  |  |  |  | Pre | 2.0 |  |  |  |  |  |  |  |  |  |  |  |  |  |  |
| H | H | H | H | (CH₃)₂CHO— | Post | 2.0 | 3C 9G 6Y | 2C 5D 9G | 1C 9G 2C 7G | 9G 2U 9G | 8H 3C 9G | 9G | 3G | &E 3C 8G | 8G | 4G | 9G | 9G | 9G | &E |
|  |  |  |  |  | Post | 2.0 |  |  |  |  |  |  |  |  |  |  |  |  |  |  |
|  |  |  |  |  | Pre | 2.0 |  |  |  |  |  |  |  |  |  |  |  |  |  |  |
| H | H | H | H | (CH₃)₂CHO— | Post | 2.0 |  | 8C 9G | 9H 2C 9H | 9G 2C 9G 9H | 9H 9C | 2G | 5G | 8G 5G | 5C 9H | 7G | 9C | 8C | 2C 7H | 7G |
|  |  |  |  |  | Pre | 2.0 |  |  |  |  |  |  |  |  |  |  |  |  |  |  |
| CH₃ | H | H | H | (CH₃)₂CHO— | Post | 2.0 | 9G 9C | 8C 9G | 9H 2C 9H | 9G 2C 9G 9H | 9H 9C | 9G 2G | 8G 5G | &E 5C 9G &E | 9H 5C 9H 2C 9H | 8G 3G | 9G 9C | 9G 9C | 9G 9C | &E 1C 7G 9G |
|  |  |  |  |  | Pre | 2.0 |  |  |  |  |  |  |  |  |  |  |  |  |  |  |
| CH₃ | H | H | H | n-C₃H₇O— | Post | 2.0 | 9C | 7C 9G | 1C 8G 9H | 5U 9G 9G | 9C 9H | 5G 9G | 1C 8G 3G 8G | 3C 8G &E | 2C 9H 9H | 2C 5G | 9G &C | 9C 9G | 3C 8G 9G | 1C 8C &E |
|  |  |  |  |  | Post | 2.0 |  |  |  |  |  |  |  |  |  |  |  |  |  |  |
|  |  |  |  |  | Pre | 2.0 |  |  |  |  |  |  |  |  |  |  |  |  |  |  |
|  |  |  |  |  | Pre | 2.0 |  |  |  |  |  |  |  |  |  |  |  |  |  |  |

Table VI—continued

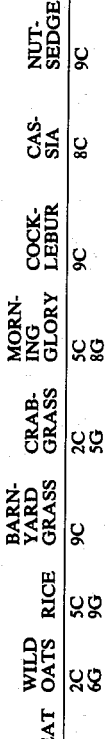

| R$_3$ | R$_6$ | X | Mode of Application | Rate Kg/Ha | BUSH BEAN | COT-TON | SOR-GHUM | CORN | SOY-BEAN | WHEAT | WILD OATS | RICE | BARN-YARD GRASS | CRAB-GRASS | MORN-ING GLORY | COCK-LEBUR | CAS-SIA | NUT-SEDGE |
|---|---|---|---|---|---|---|---|---|---|---|---|---|---|---|---|---|---|---|
| Cl | H | CH$_3$OCH$_2$— | Post | 0.4 | 9C | 6C | 5U | 9C | 2C | 1C | 2C | 5C | 9C | 2C | 5C | 9C | 8C | 9C |
|  |  |  | Post | 0.4 |  | 9G | 9G | 9G | 9G | 6G | 6G | 9G | 9H | 5G |  | 9G |  |  |
|  |  |  | Pre | 0.4 |  |  | 9H | 3C | 9H | 9H | 7G | &E |  | 7G | 8G | 9G | 9G | 8E |
| CH$_3$ | H | CH$_3$OCH$_2$— | Post | 0.4 | 6C | 5C | 2U | 9G | 9C | 3G | 8G | 5C | 9H | 1C | 5C | 9C | 6C | 9C |
|  |  |  | Post | 0.4 | 9G | 9G | 9G | 8G |  |  |  | 8G |  | 5G | 8G |  |  |  |
|  |  |  | Pre | 0.4 |  |  | 9H | &E |  |  |  | &E |  | 1C | 9G |  |  |  |
| CH$_3$O | CH$_3$O | C$_2$H$_5$O | Post | 0.4 | 9C | 3C | 2C | 2U | 9H | 2H | 1C | 6C | 6C | 4G | &C | 9G | 9C | 8E |
|  |  |  | Post | 0.4 |  | 9G | 8G | 8G |  | 8G | 8G | 8G | 8G | 7G |  |  |  |  |
|  |  |  | Pre | 0.4 |  |  | 9H | 8G | 9C | 1C | 6G | &E | 9G |  | 9C | 8G | 9C | 2C |
| Cl | H | C$_2$H$_5$O | Post | 0.4 | 9C | 3C | 9H | 8G | 9H | 7G | 7G | 7C | 8G | 5G | 9C | 5G | 8G | 9G |
|  |  |  | Post | 0.4 |  | 9G | 9G | 5U | 9G | 8G | 3G | 3C | 9C |  |  | 3C | 9C | 3G |
|  |  |  | Pre | 0.4 |  |  | 5U | 9G | 4H | 5G | 5G | &E | 9H | 1C | 9G | 8G | 5C | 9C |
| CH$_3$O | Cl | C$_2$H$_5$O | Post | 0.4 | 9C | 4C | 4U | 9G | 3C | 6G | 7G | 4C | 9H | 7G | 9C | 2C | 4C | 5G |
|  |  |  | Post | 0.4 |  | 9G | 9G | 1C | 9G |  |  | 7G |  | 5G |  |  | 9G |  |
|  |  |  | Pre | 0.4 |  |  | 1C | 9G | 9H | 8G | 8G | &E | 9H | 4G |  |  | 5G |  |
| Cl | Cl | C$_2$H$_5$O | Post | 0.4 | 7C | 6C | 8G | 1C | 3H | 5G | 0 | 2C | 9H | 3G | 9C | 6G | 8G | 5G |
|  |  |  | Post | 0.4 | 9G | 9G | 7G | 9G | 8G |  |  | 7G | 2C |  |  |  | 5C |  |
|  |  |  | Pre | 0.4 |  |  |  | 8H | 8H | 5G | 4G | &E | 9H |  | 9C | 2G | 7C | 9G |
|  |  |  | Pre | 0.4 |  |  | 7G | 9G |  | 5G | 4G | 2C | 2C | 3G |  |  | 5C | 2C |
|  |  |  | Pre | 0.4 |  |  |  |  |  |  |  | 7G | 8G | 5G | 9C | 5G | 8G | 9G |
|  |  |  | Pre | 0.4 |  |  |  |  |  |  |  | &E |  |  |  |  | 6C | 7G |

Table VI—continued

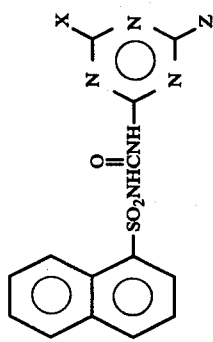

| X | Z | Mode of Application | Rate Kg/Ha | BUSH BEAN | COTTON | SORGHUM | CORN | SOYBEAN | WHEAT | WILD OATS | RICE | BARNYARD GRASS | CRAB-GRASS | MORNING GLORY | COCKLEBUR | CASSIA | NUTSEDGE |
|---|---|---|---|---|---|---|---|---|---|---|---|---|---|---|---|---|---|
| CH$_3$O | CH$_3$ | Post | 0.4 | 6C | 6C | 9U | 9C | 9C | 3G | 2G | 9C | 9H | 2G | &C | &C | 2C | 5G |
|  |  | Post | 0.4 | 9H | 9G | 9G |  | 9H | 2G | 2C | &E | 2C | 0 | 9G | 9G | 7G | 2G |
|  |  | Pre | 0.4 |  |  | 9G |  |  |  |  |  | 9H |  |  |  | 9G |  |
| CH$_3$O | CH$_3$O | Post | 0.4 | 9C | 6C | 2U | 9H | 5H | 1C | 1C | 5C | 2C | 0 | &C | &C | 5C | 2C |
|  |  | Post | 0.4 |  | 9G | 9G |  | 9G |  |  | 9G | 7H |  |  |  | 9G | 9G |
|  |  | Pre | 0.4 |  |  | 9G |  | 9H |  |  | &E | 6G |  |  |  | 9G | 0 |
| CH$_3$ | CH$_3$ | Post | 0.4 | 1B | 1C | 2G | 9G | 2H | 4G | 3G | 5G | 0 | 0 | 9G | 9G | 1C | 1C |
|  |  | Post | 0.4 | 2H | 2H | 9G | 1H | 9G | 0 | 0 |  |  |  | 3H | 9H |  | 5G |
|  |  | Pre | 0.4 | 9G | 8G | 3G |  |  |  |  |  |  |  | 9G |  |  |  |
|  |  | Pre | 0.4 |  |  | 2G | 0 | 2H | 0 | 0 | 4H | 0 | 0 | 6G | 8G | 2G | 0 |

Table VI—continued

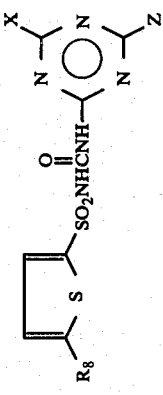

| R8 | X | Z | Mode of Application | Rate Kg/Ha | BUSH BEAN | COT-TON | SOR-GHUM | CORN | SOY-BEAN | WHEAT | WILD OATS | RICE | BARN-YARD GRASS | CRAB-GRASS | MORN-ING GLORY | COCK-LEBUR | CAS-SIA | NUT-SEDGE |
|---|---|---|---|---|---|---|---|---|---|---|---|---|---|---|---|---|---|---|
| H | CH3O | CH3O | Post | 2.0 | &D 6Y | 2C 9G | | 9G | 8H | 9G | 3G | &E | &C | 1C 7G 7G | &C | &C | 2C &P 8G | 2C 8G &E |
| | | | Post | 2.0 | | | 9G | 1U | 9H | 7G | | | 1C | | 8G | 8H | | |
| | | | Pre | 2.0 | | | | 9G 1C 3G | | | | | | | | | | |
| Cl | CH3 | CH3 | Post | 2.0 | 5S 6Y 7G | 5C 7G 5H | 1C 4G | | 7G 2C | 3G | 0 | 7G | 1G | 4G | 4G | 9C | 2G | 4G |
| | | | Pre | 2.0 | | | | | | | | | | | | | | |
| | | | Post | 2.0 | | | | | &E | 0 | 0 | 3C 7G 6G | 0 | 0 | 1C 4H 5C 9G | 1C 9G 6C 9G | 2C 4H 5C | 3C |
| Cl | CH3O | CH3O | Post | 2.0 | 1C 3G 6Y | 3C 9G | 2C | 1C 5G 1C 4G | 2C 2H | 0 | 2G | | 1G | 2G | | | | 1C 8G |
| | | | Post | 2.0 | | | 3G | | | | | | | | | | | |
| H | CH3O | CH3O | Pre | 0.4 | 2H 8G 6Y | 8C 9G | 1H 1C 9G | 6G 9H | 8H 9C | 2G 0 | 3G 2G | 9G 9C | 2C 2C 9H | 2G 6G | 9G 9C | 9G 5C 9G | 7G 7C 9G | &E 9C |
| | | | Post | 0.4 | | | | | | | | | | | | | | |
| | | | Pre | 0.4 | | | 2C 9G | 2C 9G | &E | 0 | 0 | &E | 2C 8H 9C | 1C 6G | 9G | 9G | 6C 9G | 8G |
| H | CH3 | CH3O | Post | 0.4 | 9C | 7C 9G | | 9C | 9C | 5G | 2C 4G 1C | 9C | 9G 9C | 2C 8G | &C | 5C | 9C | 6C 9G |
| | | | Post | 0.4 | | | 9G | | | | | | | | | | | |
| | | | Pre | 0.4 | | | 8G | 9C | 9G | 0 | | 8G | 9G 1C 7H | 1C | 9G | 9G | 9C | 2G |

Table VI—continued
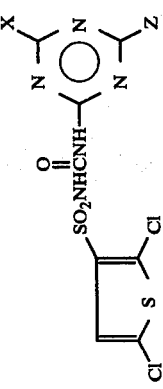
| X | Z | Mode of Application | Rate Kg/Ha | BUSH BEAN | COT-TON | SOR-GHUM | CORN | SOY-BEAN | WHEAT | WILD OATS | RICE | BARN-YARD GRASS | CRAB-GRASS | MORN-ING GLORY | COCK-LEBUR | CAS-SIA | NUT-SEDGE |
|---|---|---|---|---|---|---|---|---|---|---|---|---|---|---|---|---|---|
| CH$_3$O | CH$_3$O | Post | 0.4 | 4G | 6C | 2G | 0 | 4C | 0 | 0 | 0 | 0 | 0 | 4C | 5G | 2C | 5G |
|  |  | Post | 0.4 |  | 9G | 2G | 2G | 8G | 0 | 0 | 4G | 0 | 2G | 9G | 4G | 3G | 8E |
|  |  | Pre | 0.4 |  |  | 5G | 2G | 8H | 0 | 0 | 2G | 2C | 0 | &C | 5C | 2C | 2C |
| CH$_3$ | CH$_3$O | Post | 0.4 | 2C | 2C |  |  | 2H |  |  |  |  |  |  | 9G |  | 8G |
|  |  | Post | 0.4 | 8G | 7G |  |  | 5G |  |  |  |  |  |  |  |  |  |
|  |  | Pre | 0.4 | 6Y |  | 5G | 6G | 9H | 4G | 2G | 9H | 2G | 2G | 9G | 8G | 7G | 9G |

Table VI—continued

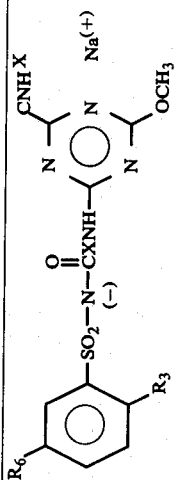

| R3 | R6 | X | Mode of Application | Rate Kg/Ha | BUSH BEAN | COT-TON | SOR-GHUM | CORN | SOY-BEAN | WHEAT | WILD OATS | RICE | BARN-YARD GRASS | CRAB-GRASS | MORN-ING GLORY | COCK-LEBUR | CAS-SIA | NUT-SEDGE |
|---|---|---|---|---|---|---|---|---|---|---|---|---|---|---|---|---|---|---|
| Cl | H | CH3 | Post | 0.4 | 5C 9G 6Y | 9C | 8U 9G | 9U 9G | 9C | 1C 8G | 2C 5G | 4C 8G | &C | 9C | 9C | 9C | 9C | &C |
|  |  |  | Post | 0.4 |  |  |  |  |  |  |  |  |  |  |  |  |  |  |
|  |  |  | Pre | 0.4 |  |  | &E | &E |  |  |  |  |  |  |  |  |  |  |
| Cl | H | CH3O | Post | 0.4 | 9C |  | 3U 9H | 5U 9H | 9C | 9G | 2C 6G 3G | 3C 8G | 9H | 9H | &E | 9G | 9G | &E |
|  |  |  | Post | 0.4 |  | 5C 9G |  |  | 9C |  |  |  | 6C 9H |  | &C |  | 9C | 9C |
|  |  |  | Pre | 0.4 |  |  | 9H | 9H | 9H | 5G |  | &E | 9H | 3C 8G 9H | &C | 9C | 9C | &E |
|  |  |  | Pre | 0.4 |  |  |  |  |  |  |  |  |  |  |  |  |  |  |
| CH3 | NO2 | CH3 | Post | 2.0 | 2C 8G 6Y | 5C 9G | 9C | 9C | 5C 8G | 7G | 2C 8G 8C | 5C 7G | &C | 9C | 5C 8G | 3C 9G | 5C 8G | 9C |
|  |  |  | Post | 2.0 |  |  |  |  |  |  |  |  |  |  |  |  |  |  |
|  |  |  | Pre | 2.0 |  |  | 9H | 9G | 9H | 9H | 3C 7G | &E | 9H | 5C 9G | 9G | &E | 9G | 9G |
|  |  |  | Pre | 2.0 |  |  |  |  |  |  |  |  |  |  |  |  |  |  |

Utility of the compounds of the invention for selective weed control in wheat was first observed in a number of greenhouse tests. The four tests described below (A, B, C and D) illustrate that utility.

TEST A

Two 25 cm - diameter plastic bulb pans were filled with fertilized and limed Fallsington silt loam soil. One pan was planted with corn, sorghum and several grassy weeds. The other pan was planted with soybeans, purple nutsedge (*Cyperus rotundus*), and several broadleaf weeds. The following grassy and broadleaf species were planted: carbgrass (*Digitaria sanguinalis*), barnyardgrass (*Echinochloa crusgalli*), wild oats (*Avena fatua*), johnsongrass (*Sorghum halepense*), giant foxtail (*Setaria faberii*), Kentucky bluegrass (*Poa pratensis*), cheatgrass (*Bromus secalinus*), mustard (*Brassica arvensis*), cocklebur (*Xanthium pennsylvanicum*), pigweed (*Amaranthus retroflexus*), curly indigo (*Aeschynomene virginica*), morningglory (*Ipomoea hederacea*), Cassia (*Cassia tora*), teaweed (*Sida spinosa*), velvetleaf (*Abutilon theophrasti*), and jimsonweed (*Datura stramonium*). In addition, two 12.5 cm - diameter paper cups were filled with prepared soil; one was planted with rice and wheat, the other with sugarbeets. The above four containers were treated preemergence, i.e., the compounds were sprayed on the soil surface before seed germination.

Twenty-eight days after treatment, the plants were evaluated. The data obtained are summarized in Table VII. It should be noted that wheat has more tolerance for the compounds tested than most weed species.

TABLE VII
PREEMERGENCE APPLICATIONS TO FALLSINGTON SILT LOAM

| Structure | Rate, kg/ha | Crab grass | Barn-yard-grass | Sor-ghum | Wild Oats | John-son-grass | Giant Fox-tail | Ky. Blue-grass | Cheat-grass | Corn | Mus-tard | Cock-le-bur | Pig-weed |
|---|---|---|---|---|---|---|---|---|---|---|---|---|---|
| Structure 1 (2,5-dimethoxyphenyl; 4,6-dimethoxy pyrimidine) | 0.06 | 2G | 5G | 8G 5H | 3G | 8G 5H | 0 | 7G 5H | 7G | 0 | 8G | 6G 3H | 10C |
| | 0.25 | 5G | 9G 8H | 9G 10H | 7G 3H | 8C 5H | 2G 3H | 10H | 10H | 9G 9H | 10C | 8G 5H | 10C |
| Structure 2 (2-chlorophenyl; 4-methoxy-6-methyl pyrimidine) | 0.03 | 8H 8G | 9H 9G | 8H 9G | 2G 0 | 7H 7G | 8H 8G | 8H | 4H | 10H 8G | 10H | 8G 7G | 10H |
| | 0.06 | 5H | 5H | 9H | 5G | 7H | 5H | 10E | 5G | 5H | 10C | 3H | 10C |
| Structure 3 (2-thienyl; 4-methoxy-6-methyl pyrimidine) | 0.12 | 8G 8H | 9H | 10H | 3G 5G 3H | 8H | 9H | 8H | 6H | 10H | 10H | 8G 3H | 10H |
| | 0.25 | 10H | 10H | 10H | 4G 3C 6G | 9G 9H | 10H | 10E | 7G | 10H | 10C | 7G 3H 8G | 10C |
| | 0.50 | 9H | 7G | 7G | 3C | 8H | 9H | 9H | 8H | 10H | 10C | 8H | 10H |
| Structure 4 (2,5-dimethoxyphenyl; 4-methoxy-6-methyl pyrimidine) | 0.12 | 6G | 4C 9C | 4C 8G 4C | 3G 3G | 5G 6G | 6G 8G | 5G 7G | 3G 3C 6G 6C | 10C 10C | 10C 10C | 7G 3H 8G 10C 9C | 10C 10C |
| | 0.50 | 2C 8G 4C | 9C | 4C | 3G | 6G | 8G | 7G | 6C | 10C | 10C | 9C | 10C |
| Structure 5 (2-chloro-5-methoxyphenyl; 4,6-dimethoxy pyrimidine) | 0.6 | 5G | 9G 8H | 8G | 3G | 5G 3H | 0 | 8G | 6G | 8G 5H | 8G | 8G 5H | 10C |
| | 0.25 | 7G | 10H | 10H | 6G | 8G 8H | 6G | 9G | 8G | 10H | 10H | 9G 9C | 10C |
| | 0.06 | 0 | 4G 8G 8H | 5G 8G 8H | 0 | 2G 6G 3H | 0 | 5G | 3G | 5G 7G 3H | 8G | 7G 3H 7G | 10C |
| | 0.25 | 4G | 8H | 10H | 3G | 3H | 2G | 10E | 6G | 3H | 10C | 5H | 10C |

TABLE VII-continued

| Structure | Rate, kg/ha | Nut-sedge | H. Indigo | Morn-ing glory | Cas-sia | Tea-weed | Vel-vet-leaf | Jim-son weed | Soy-bean | Rice | Wheat | Sugar-beets |
|---|---|---|---|---|---|---|---|---|---|---|---|---|
|  | 0.06 | 5G | | | | | | | 5G | | | |
| | 0.12 | 5H 7G | | 2H 6G | | | | | 5H 7G | 8H | 6C | 10H |
| | 0.50 | 7H 8G | | 3H 6G | | 3H | 6H | 3H | 7H 8G | 10H | 5G | 10H |
| | | 8H | | 5H | | 8H | 8H | 5H | 8H | 10H | 8G | 10H |
|  | 0.06 | 4G | 6G | 7G | 8G | 5G | 0 | 7G 8G | 7G | 8G | 0 | 7G |
| | 0.25 | 8G | 5H | 5H | 5C 9G | 5H 8G | 6G | 5H | 7H 9G | 8H | 4G | 7H 9G |
| 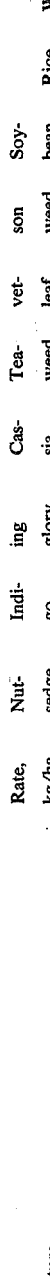 | | | 10C | 10C | 8C | 7H | 5H | | 9H | 10H | | 9H |
| 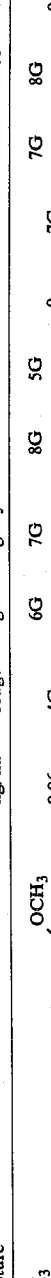 | 0.03 | 6G | — | 9H | 10H 8G | 10C | 10H | 8H | 9H | 8H | 2G | 10H |
| | 0.06 | 5G | 10C | 7G | 9C | 10C | 10C | 9C | 8G | 10H | 0 | 9G |
| | 0.12 | 7G | 10H | 8G | 8H | 10H | 10H | 8G | 9G | 9G | 4G | 10H |
| | 0.25 | 7G | 10C | 9H 9C | 10C | 10C | 10C | 5H 10C | 8H 8G | 9H 10H | 0 | 9C |
| | 0.50 | 8G | 10H | 8C 8H | 10H | 10H | 10H | 9G 5H | 9G 5H | 9H 10E | 5G 5H | 9H |
| 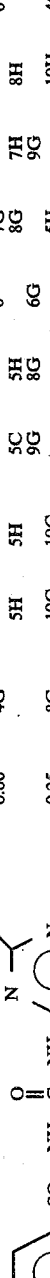 | 0.12 | 6G | 10C | 8G | 9C | 9C | 9C | 5H 10C | 8G | 2G | 3G | 10C |
| | 0.25 | 8G | 10C | 8G | 9C | 9C 10C | 9C | 3C 8G | 5H 8G | 7G | 3C | 10C |
| | | | | 4H | 8C 10C | | | 5C | 8H | | | |
|  | 0.06 | 5G | 10E | 10C | 8G | 9G | 9G | 7G | 7G | 10H | 0 | 9G |
| | 0.25 | 8E 5G | 10E | 10C | 8C 10C | 9C 10C | 9C 10C | 8G | 8G | 10H | 2G | 10C |

TABLE VII-continued

| Structure | | | | | | | | | | | | | |
|---|---|---|---|---|---|---|---|---|---|---|---|---|---|
| ![structure with OCH3, OCH3, SO2-NH-C(=O)-NH-, pyrimidine with 2 OCH3, Cl on phenyl] | 0.06 | 7G | 4G | 8G | 8G | 8G | 10C | 8G | 7G | 7G | 5G | 0 | 9G |
| | 0.25 | 10E | 10C | 9G | 8H 10H | 10C | 10C | 5H 10C | 8G | 5H 8G | 5H 10H | 0 | 9G |
| ![structure with OCH3, SO2-NH-C(=O)-NH-, pyrimidine with 2 OCH3, Cl on phenyl] | 0.06 | 5G | 10H | 8G | 10H | 10H | 9H | 8H | 7G | 9G | 8G | 0 | 8H |
| | 0.12 | 5H 7G | 9H | 5H 8G | 9H | 9H | 8H | 9H | 5H 8G | 8H 9G | 8H 9G | 3G | 9H |
| | 0.50 | 10E | 10H | 5H | 10H | 10H | 10H | 10H | 5H | 9H | 9H | 4G | 10H |

TEST B

Twenty-five cm - diameter plastic pots filled with Fallsington silt loam were planted with soybean, cotton, alfalfa, corn, rice, wheat, sorghum, velvetleaf (*Abutilon theophrasti*), sesbania (*Sesbania exaltata*), Cassia (*Cassia tora*), morningglory (*Ipomoea* sp.), jimsonweed (*Datura stramonium*), cocklebur (*Xanthium pennsylvanicum*), crabgrass (*Digitaria* sp.), nutsedge (*Cyperus rotundus*), barnyardgrass (*Echinochloa crusgalli*), giant foxtail (*Setaria faberii*) and wild oats (*Avena fatua*). Approximately 2½ weeks after planting, the young plants and the soil around them were sprayed overall with the test chemicals dissolved in a nonphytotoxic solvent. Fourteen days after treatment, all species were compared to untreated controls and visually rated for response to treatment. The data are presented in Table VIII.

TABLE VIII

OVER-THE-TOP SOIL/FOLIAGE TREATMENT

| Structure | Rate, kg/ha | Soy-beans | Vel-vet-leaf | Ses-bania | Cas-sia | Cot-ton | Morn-ing-glory | Al-fal-fa | Jim-son-weed | Coc-kle-bur | Corn | Crab-grass | Rice | Nut-sedge | Barn-yard-grass | Wheat | Giant Fox-tail | Wild Oats | Sor-ghum |
|---|---|---|---|---|---|---|---|---|---|---|---|---|---|---|---|---|---|---|---|
|  | 0.06 | 10G | 7G | 10G | 8G | 8G | 10G | 10G | 10G | — | 6G | 0 | 6G | 2G | 8G | 3G | 3G | G | 8G |
|  | 0.25 | 5B 10G | 3C 10G | 9C 10G | 5C 10G | 5C 10G | 9C | 6C 10G | 10G 10G | 10G | 2C 6G | 3G | 2C 3G | 5G | 2H 6G | 3G | 3G | 6G 2B | 3C 10G |
|  |  | 6B | 8C | 9C | 6C | 6C | 10C | 7C | 4C | 5C | 3C | | 3C | 5C | 2C | 3G | 3G | | 5C |
|  | 0.06 | 10G | 10G | 10G | 10G | 10G | 10G | 10G | 10G | 10G | 7G | 5G | 10G | 3C | 8G | 2G | 3G | 2G | 8G |
|  | 0.25 | 7C 10G | 7C | 9C 10G | 7C 10G | 4C 10G | 9C | 7C 10G | 9G 10G | 9C | 3C 9G | 8G | 3C 10G | 10G | 10G | 7G | 7G | 10G | 6G |
|  |  | 7C | | 9C | 5C | 4C | 7C | 9C | 6C | 10C | 6C | | 5C | 9C | 8C | | | | |
|  | 0.06 | 10G | 10G | 5G | 10G | 10G | 10G | 10G | 10G | 5G | 10G | 0 | 4C | 5G | 2G | 0 | 0 | 0 | 6G |
|  | 0.25 | 8G 10G | 7C | 3C 10G | 10G | 2C 10G | 8G | 3C 10G | 8C | 6C 10G | 8C | 4G | 7C | 10G | 8G | 3G | 10G | 5G | 5H 10G |
|  |  | 9C | 9C | 9C | 9C | 7C | 10C | 7C | 10C | 7C | 10C | | 7C | 7C | 6C | 0 | 10G | 0 | 8H |
| 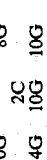 | 0.06 | 10G | 10G | 10G | 10G | 5G | 10G | 3G | 7G | 10G | 6G | 0 | 0 | 0 | 2G | 0 | 0 | 0 | 6G |
|  | 0.12 | 8C 10G | 7C 10G | 9C 10G | 6C 10G | 2C 10G | 8C | 3C 10G | 3C 10G | 6C 10G | 5H 7G | 2G | 3G | 0 | 8G | 3G | 2G | 5G | 5H 10G |
| 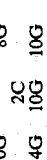 | 0.50 | 7C | 8C | 10C | 9C | 7C | 10C | 7C | 5C | 7C | 3C | | 5G 4G | 2G | 3H | 4G | 10G | 0 | 7H |
| 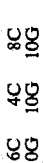 | 0.06 | 8C | 10G | 10G | 10G | 6G | 9C | 2C 8G | 8G | 10G | 9G 6G | 0 | 5C | 3G | 5G 7G | 0 | 5G 5G | 4G | 6G 4C 7G |
|  | 0.25 | 6B 10G | 8C | 7C 10G | 3C 10G | 7G 9G | 10C | 4C | 10G | 10G | 6G | 0 | 8G | 2C 5G | 3H 7G | 6G 2H | 6C 0 | 7G 4G | 5C 8G 6C 8G |
| 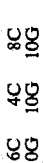 |  | 6B | 8C | 9C | 5C | 6C | 10C | 4C | 3C | 9C | 2C | | 4C | 3C | 5H | 3G | 0 | 4G | 2C 7G 3C |

TABLE VIII-continued

OVER-THE-TOP SOIL/FOLIAGE TREATMENT

| Structure | Rate, kg/ha | Soy-beans | Vel-vet-leaf | Ses-bania | Cas-sia | Cot-ton | Morn-ing-glory | Al-fal-fa | Jim-son-weed | Coc-kle-bur | Corn | Crab-grass | Rice | Nut-sedge | Barn-yard-grass | Wheat | Giant Fox-tail | Wild Oats | Sor-ghum |
|---|---|---|---|---|---|---|---|---|---|---|---|---|---|---|---|---|---|---|---|
| Structure 1 (CH₃, Cl-phenyl) | 0.06 | 10G | 10G | 10G | 6G | 5G | 8G | 10G | 10G | 10G | 9G | 0 | 8G | 0 | 6G | 3G | 9G | 0 | 5G |
| | 0.12 | 6C 10G | 7C 10G | 8C 10G | 2C 7G | 3C 7G | 5C 10G | 5C 10G | 8C 10G | 2C 10G | 8C 9G | 4G | 8C 7G | 5G | 3C 5G | 5G | 2C 9G | 0 | 3C 7G |
| | 0.50 | 5C 10G | 8C 10G | 7C 10G | 3C 9G | 3C 10G | 9C 10G | 6C 10G | 8C 10G | 6C 10G | 8C 9G | 4G | 5C 8G | 2G | 2C 9G | 7G | 4C 9G | 0 | 5C 7G |
| Structure 2 (CH₃/OCH₃, Cl-phenyl) | 0.06 | 6C 10G | 9C 10G | 9C 10G | 5C 10G | 6C 10G | 9C 10G | 6C 5G | 5C 10G | 8C 10G | 9C 5G | 0 | 5C | 0 | 8C | 2C | 6C | 4G | 5C |
| | 0.12 | 8C 10G | 8C 10G | 8C 10G | 6C 10G | 5C 10G | 8C 10G | 1C 10G | 5C 10G | 2C 10G | 2C 7G | 0 | 0 | 2G | 3H | 0 | 0 | 0 | 4G |
| | 0.50 | 8C 10G | 9C 10G | 9C 10G | 7C 10G | 5C 10G | 9C 10G | 3C 10G | 6C 10G | 5C 10G | 6C 8G | 0 | 0 | 4G | 4G | 0 | 0 | 0 | 4G |
| Structure 3 (OCH₃/OCH₃, thienyl) | 0.12 | 7C 10G | 9C 10G | 9C 10G | 7C 10G | 6C 6G | 9C 10G | 4C 10G | 7C 10G | 7C 10G | 7C 5G | 2G | 2C | 3C | 3H 7G | 0 | 0 | 0 | 6G |
| | 0.12 | 6C 10G | 8C 10G | 7C 10G | 3G | 2C 10G | 5C 10G | 10G | 2C 10G | 6C 10G | 5H 7G | 0 | 0 | 3G | 3H 8G | 0 | 0 | 0 | 2C 2G |
| | 0.50 | 6C | 9C | 7C | 3C | 2C | 5C | 10G | 9C | 7C | 7H | 2G | 0 | 5G | 3H 8G | 2G | 0 | 0 | 2C 4G |
| | 0.50 | 6C | 9C | 7C | 3C | 2C | 5C | 10G | 9C | 7C | 7H | 2G | 0 | 5G | 2H | — | 0 | 0 | 2C |

TEST C

The compounds were applied in a non-phytotoxic solvent as overall postemergence sprays on plantings of wheat (11 cm tall, 2 leaf stage), wild oats (Avena fatua) (9 cm tall, 1 leaf stage), *Bromus tectorum* (5 cm tall, 1 leaf stage), *B. secalinus* (5 cm tall, 1 leaf stage), blackgrass (*Alopecurus myosuroides*) (3 cm tall, 1 leaf stage), and annual ryegrass, (*Lolium multiflorum*) (8 cm tall, 1 leaf stage) and also preemergence on plantings of the same species. All plantings were in 25 cm diameter soil pans. The tests were maintained in a greenhouse and plant response ratings were taken 5 weeks after application. The results of these tests are shown in Table IX.

TABLE IX

| Structure | Rate kg ai/ha | Preemergence |||||| 
|---|---|---|---|---|---|---|---|
| | | Wheat | Wild Oats | Bromus tectorum | Bromus secalinus | Blackgrass | Annual Ryegrass |
| 2-Cl-C6H4-SO2-NH-C(O)-NH-C(triazine with 2 OCH3) | 1/32 | 0 | 0 | 0 | 4G | 5G | 5G |
| | 1/16 | 0 | 0 | 0 | 4G | 5G | 5G |
| | 1/8 | 0 | 1C | 1G | 7G | 7G2C | 6G2C |
| 3-Cl-C6H4-SO2-NH-C(O)-NH-C(triazine with 2 OCH3) | 1/32 | 0 | 0 | 0 | 1G | 2G | 5G |
| | 1/16 | 0 | 0 | 0 | 3G | 3G | 5G |
| | 1/8 | 0 | 1G | 0 | 5G | 7G | 8G2C |
| (H3CO)2-triazine-C-NH-C(O)-NH-SO2-thiophene | 1/32 | 0 | 0 | 0 | 0 | 0 | 0 |
| | 1/16 | 0 | 0 | 0 | 1G | 1G | 0 |
| | 1/8 | 0 | 0 | 0 | 5G | 6G | 6G1C |
| (H3CO)(H3C)-triazine-C-NH-C(O)-NH-SO2-(2-Cl-C6H4) | 1/32 | 1C | 0 | 5G | 5G | 8G | 6G1C |
| | 1/16 | 2C | 2C | 8G | 8G | 9G | 9C |
| | 1/8 | 3C | 3C | 9G | 9G3C | &C | 9C |
| (H3CO)(H3C)-triazine-C-NH-C(O)-NH-SO2-(2-Cl-5-OCH3-C6H3) | 1/32 | 0 | 1G1C | 6G | 6G | 7G1C | &C |
| | 1/16 | 0 | 3G1C | 6G | 7G | 9G2C | 9C |
| | 1/8 | 2C | 4G1C | 8G | 9G | 9G | &C |
| (H3CO)2-triazine-C-NH-C(O)-NH-SO2-(2,5-(OCH3)2-C6H3) | 1/32 | 1G | 5G | 8G | 9G | 9G | &C |
| | 1/16 | 1G | 5G | 9C | &C | 9C | &C |
| | 1/8 | 2G | 5G | 9G2C | 9C | 9C | &C |
| (2-Cl-C6H4)-SO2-NH-C(O)-NH-C(pyrimidine 2,6-di-CH3) | 1/32 | — | 0 | 4G | 9C | 8G | &C |
| | 1/16 | 4G | 0 | 8G | 9C | 9G | &C |
| | 1/8 | 4G | 0 | 8G | &C | 8G | &C |

| Structure | Rate kg ai/ha | Postemergence |||||| 
|---|---|---|---|---|---|---|---|
| | | Wheat | Wild Oats | Bromus tectorum | Bromus secalinus | Blackgrass | Annual Ryegrass |

TABLE IX-continued

| Structure | Rate | Wheat | Wild Oats | Bromus tectorum | Bromus secalinus | Barley | Kochia | Matricaria | Wild Mustard | Dog Fennel | Wild Buckwheat |
|---|---|---|---|---|---|---|---|---|---|---|---|
|  | 1/32<br>1/16<br>1/8 | | 0<br>3G<br>3G1C | 0<br>1G<br>1G1C | 2G<br>5G<br>8G3C | 6G<br>8G<br>9G | 8C<br>&C<br>&C | 8G<br>9C<br>9C | | | |
| 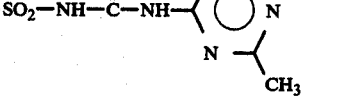 | 1/32<br>1/16<br>1/8 | | 1G<br>1G<br>1G | 0<br>2G<br>2G | 5G<br>8G<br>9G2C | 8G3C<br>9C<br>9G3C | 7G<br>9G<br>9G | &C<br>&C<br>&C | | | |
| 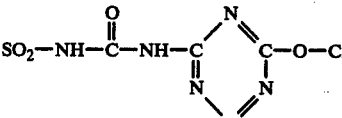 | 1/32<br>1/16<br>1/8 | | 0<br>0<br>1G | 0<br>0<br>2G | 0<br>0<br>3G | 0<br>2G<br>5G | 3G<br>4G<br>7G | 3G<br>5G1C<br>6G | | | |
| 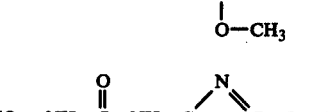 | 1/32<br>1/16<br>1/8 | | 0<br>1G<br>0 | 1G<br>0<br>0 | 0<br>0<br>0 | 1G<br>2G<br>6G | 3G<br>4G<br>5G | 6G<br>7G<br>7G | | | |
| 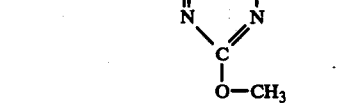 | 1/32<br>1/16<br>1/8 | | 1G<br>1G<br>3G | 3G<br>3G<br>4G | 6G<br>6G<br>9C | 4G<br>7G<br>9C | 8C<br>&C<br>8C | 8C<br>9C<br>9C | | | |
| 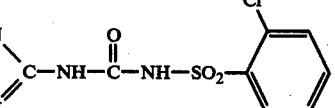 | 1/32<br>1/16<br>1/8 | | 0<br>1G<br>2G | 2G<br>3G<br>6G | 6G<br>9G<br>9G | 7G<br>9G<br>9G | 8C<br>9C<br>9C | 9C<br>9C<br>&C | | | |
| 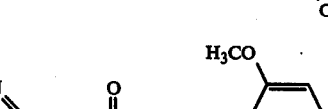 | 1/32<br>1/16<br>1/8 | | 0<br>0<br>0 | 0<br>0<br>0 | 0<br>0<br>0 | 0<br>0<br>2G | 1G<br>2G<br>2G | 3G<br>5G<br>6G | | | |

TEST D

The compounds were applied in a non-phytotoxic solvent as overall sprays to established (postemergence) plantings of wheat 22 cm tall, wild oats (*Avena fatua*) 14 cm tall, downy brome (*Bromus tectorum*) 3 cm tall, cheat (*Bromus secalinus*) 5 cm tall, barley 22 cm tall, kochia (*Kochia scoparia*) 5 cm tall, wild chamomile (*Matricaria inodora*) 3 cm tall, wild mustard (*Brassica arvensis*) 7 cm tall, dog fennel (*Eupatorium capillifolium*) 3 cm tall, and wild buckwheat (*Polygonum convolvulus*) 6 cm tall and to preemergence plantings of the same species, all planted in pots containing soil. The tests were maintained in a greenhouse, and plant response ratings were taken four weeks after application, giving the results set forth in Table X.

TABLE X

| | | | | Preemergence | | | | | | | |
|---|---|---|---|---|---|---|---|---|---|---|---|
| Structure | Rate, kg ai/ha | Wheat | Wild Oats | Bromus tectorum | Bromus secalinus | Barely | Kochia | Matricaria | Wild Mustard | Dog Fennel | Wild Buckwheat |

TABLE X-continued

| Structure | Rate | | | | | | | | | |
|---|---|---|---|---|---|---|---|---|---|---|
| (H₃CO, C-N, C=N, H₃C triazine)–NH–CO–NH–SO₂–(2-Cl-phenyl) | 1/16 | 0 | 0 | 7G | 5G | 3G3C | &C | &C | &C | &C | 9C |
| | 1/8 | 1G | 2G | 7G | 8G | 3G3C | &C | &C | &C | &C | &C |
| | 1/4 | 3G | 2G | 8G | 8G | 3G3C | &C | &C | &C | &C | &C |
| | 1/2 | 4G | 2G | 9G | 9G | 6G3C | &C | &C | &C | &C | &C |
| (H₃CO, C-N, C=N, H₃CO triazine)–NH–CO–NH–SO₂–(thiophene) | 1/16 | 0 | 0 | 0 | 0 | 0 | 8G | 9C | &C | 9C | 9C |
| | 1/8 | 0 | 0 | 0 | 0 | 0 | 8G | 9C | &C | 9C | 9C |
| | 1/4 | 1C | — | 0 | 0 | 0 | 9G | &C | &C | 9C | 9C |
| | 1/2 | 1C | 2G | 8C | 2G | 0 | 9G | 9C | &C | 9C | 9C |
| (H₃CO, C=N, N, C-N, H₃C triazine)–NH–CO–NH–SO₂–(2-Cl-5-OCH₃-phenyl) | 1/16 | 0 | 4G1C | 7G | 7G | 4G | 9C | 9C | &C | 9C | &C |
| | 1/8 | 0 | 4G1C | 7G | 7G | 4G | &C | &C | &C | 9C | &C |
| | 1/4 | 2C | 8G1C | 9C | 8G | 6G | &C | 9C | &C | 9C | 9C |
| | 1/2 | 2C | 8G1C | &C | 9C | 8G | &C | 9C | &C | &C | &C |

| | | | | Postemergence | | | | | | |
|---|---|---|---|---|---|---|---|---|---|---|
| Structure | Rate, kg ai/ha | Wheat | Wild Oats | Bromus tectorum | Bromus secalinus | Barely | Kochia | Matricaria | Wild Mustard | Dog Fennel | Wild Buckwheat |
| (H₃CO, C-N, C=N, H₃C triazine)–NH–CO–NH–SO₂–(2-Cl-phenyl) | 1/16 | 0 | 0 | — | 2G | 0 | &C | &C | &C | &C | &C |
| | 1/8 | 3G | — | — | 6G | 0 | &C | &C | &C | &C | &C |
| | 1/4 | 4G | 3G | — | 8G | 3G | &C | &C | &C | &C | &C |
| | 1/2 | 4G | 4G | — | 8G | 3G5C | &C | &C | &C | &C | &C |
| (H₃CO, C-N, C=N, H₃CO triazine)–NH–CO–NH–SO₂–(thiophene) | 1/16 | 0 | 0 | 0 | 0 | 0 | &C | &C | &C | &C | &C |
| | 1/8 | 0 | 0 | — | 2G | 0 | 8C | &C | &C | &C | &C |
| | 1/4 | 0 | 0 | — | 5G | 0 | 9C | &C | &C | &C | &C |
| | 1/2 | 0 | 0 | 0 | 5G | 2G | &C | &C | &C | &C | &C |
| (H₃CO, C=N, N, C-N, H₃C triazine)–NH–CO–NH–SO₂–(2-Cl-5-OCH₃-phenyl) | 1/16 | 0 | 0 | 6G | 8G | 2G | &C | &C | &C | &C | &C |
| | 1/8 | 0 | 3G | 6G | 8G | 2G | &C | &C | &C | &C | &C |
| | 1/4 | 0 | 3G | 9G | 8G | 2G | &C | &C | &C | &C | &C |
| | 1/2 | 2G | 6G | &C | &C | 7C | &C | &C | &C | &C | &C |

The following test illustrates the utility of these compounds for the control of aquatic weeds. The compounds were applied in a non-phytotoxic solvents as an overall spray to small ponds containing water hyacinth (*Eichornia crassipes*) plants about 25 to 30 cm tall. The tests were maintained in a greenhouse, and plant response ratings were taken four weeks after application. Results of these tests are given in Table XI.

TABLE XI

| Structure | Rate kg ai/ha | Plant Response Ratings Water Hyacinth |
|---|---|---|
| (2-Cl-phenyl)–SO₂–NH–CO–NH–(4,6-dimethylpyrimidin-2-yl) | 1/32 | 9G |
| | 1/16 | 9G |

TABLE XI-continued

| Structure | Rate kg ai/ha | Water Hyacinth |
|---|---|---|
| 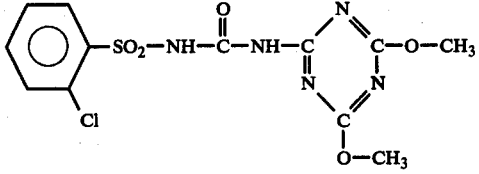 | 1/32 | 9G9C |
| 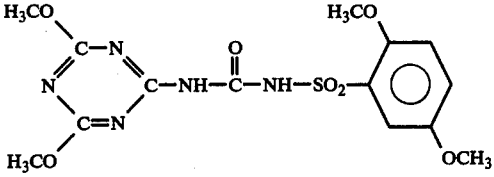 | 1/32 | &G |
| 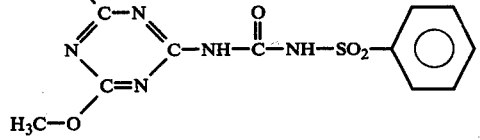 | 1/32 | 8G |
| 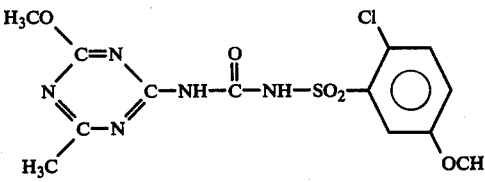 | 1/32 | &G&C |
| 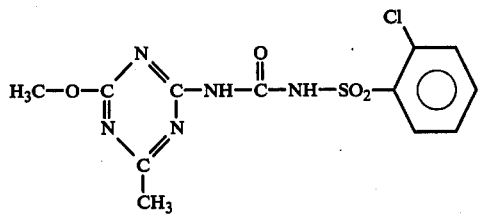 | 1/32<br>1/16 | 9G7C<br>9G7C |

The following test illustrates the utility of these compounds for the control of nutsedge.

Nutsedge (*Cyperus rotundus*) tubers (5 per pot) were planted approximately 2.5 cm deep in 10 cm pots containing Fallsington silt loam soil. Each compound to be evaluated was applied as a preemergence soil surface spray, a directed tuber spray, soil incorporated throughout the top 2.5 cm of soil and sprayed postemergence on the foilage of plants approximately 8-10 cm tall. The compounds were dissolved in a suitable solvent and applied at a spray volume of 560 l/ha. The effects of chemical treatment on plant growth were visually evaluated four weeks after treatment. The results of these tests are given in Table XII.

TABLE XII

| Structure | Rate, kg/ha | Plant Response 4 Weeks after Treatment | | | |
|---|---|---|---|---|---|
| | | Pre surface spray | Pre tuber + soil spray | Pre soil inc. 2.5 cm. | Post foliar spray |
| 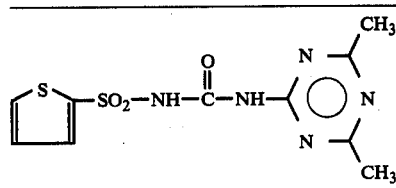 | 1/2<br>2 | 4G<br>9E,9G | 5E,5G<br>10E | 7E,7G<br>10E | 10C<br>10C |

TABLE XII-continued

| Structure | Rate, kg/ha | Plant Response 4 Weeks after Treatment | | | |
|---|---|---|---|---|---|
| | | Pre surface spray | Pre tuber + soil spray | Pre soil inc. 2.5 cm. | Post foliar spray |
| CH3-, CH3-, CH3- phenyl-SO2-NH-C(O)-NH-pyrimidine(CH3, OCH3) | 1/8<br>1/4 | 5E,8G<br>7E,8G | 8E,9G<br>10E | 9E,9G<br>10E | 7C,7G<br>7C,8G |
| Cl, OCH3 phenyl-SO2-NH-C(O)-NH-pyrimidine(OCH3, OCH3) | 1/16<br>1/8 | 3G<br>8G | 7G<br>8G | 8G<br>8G | 10C<br>10C |
| phenyl-SO2-NH-C(O)-NH-pyrimidine(OCH3, OCH3) | 1/2<br>2 | 5E,8G<br>10E | 9E,9G<br>10E | 10E<br>10E | 7C<br>10C |

PLANT GROWTH REGULANT USES

In addition to their use as herbicides, compounds of Formula I are useful as agents to beneficially modify growth of selected plant species. Rates (usually 0.01 to 1.0 kg/ha) and timing of application are selected according to species to achieve desirable effects with a minimum of phytotoxicity. Both vegetative and reproductive growth may be controlled. Examples below illustrate the response of sugarcane and sorghum to compounds of this invention. In sugarcane and sorghum, a "chemical ripening" effect is produced which results in a greater yield of soluble solids (mostly sugars). In many other grasses, growth and seed stalk development are restricted by these compounds which reduces mowing requirements. These compounds also are useful for growth control of woody and herbaceous broadleaf plants.

EXAMPLE A

Dwarf sugarcane plants, 6–8 months old, grown 3–5 stalks (1.5–3 meters tall) per 25 cm pot were sprayed with the compounds given below (2 pots per compound). Each stalk was measured to the highest visible leaf collar at the start and end of the study to determine effects on growth in height. When stalks were harvested, 5 weeks after treatment, juice was extracted therefrom and soluble solids determined at the centers of the top, middle and bottom thirds of each stalk. In stalks treated with compounds of this invention, soluble solids were increased and growth was restricted as compared to the solvent control (500 l/ha water plus surfactant Tween 20 ® at 0.2%). Results of this test are shown in Table XIII.

TABLE XIII

| | Kg/Ha | Growth (cm) | Sections of Sugarcane Stalks | | |
|---|---|---|---|---|---|
| | | | Bottom | Middle | Top |
| Cl-phenyl-SO2-NH-C(O)-NHC-triazine(OCH3, CH3) | 0.25<br>1.0 | 3<br>4 | 19.9<br>18.8 | 20.2<br>19.9 | 16.8<br>16.6 |
| Solvent control | — | 40 | 16.7 | 13.8 | 6.1 |

EXAMPLE B

Tracy sweet sorghum plants grown one per 15 cm pot to a stage just prior to head emergence were sprayed with compounds given below. Visual effects were noted about 3 weeks after spraying, then at 4 weeks plants were harvested and soluble solids determined at the centers of the top, middle, and bottom thirds of each stalk. Percent soluble solids was increased and growth and flowering were restricted. Data from this test are shown in Table XIV.

TABLE XIV

| Compound | Kg/Ha | 3-Week Response Rating* | Soluble Solids Expressed as % of Control Values in Various Sections of Sorghum Stalks | | |
|---|---|---|---|---|---|
| | | | Bottom | Middle | Top |
| 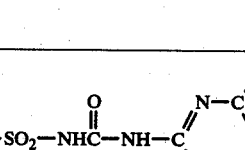 | 0.125 | 5G,F,2X | 116 | 107 | 101 |
| | 0.5 | 8G,F | 115 | 107 | 113 |
| | 2.0 | 8G,F | 118 | 107 | 113 |
| 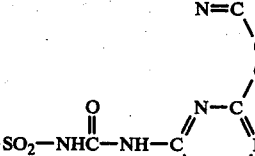 | 0.125 | 8G,F,3X | 128 | 123 | 118 |
| | 0.5 | 9G,F | 143 | 124 | 105 |
| | 2.0 | 9G,F | 127 | 111 | 132 |
| 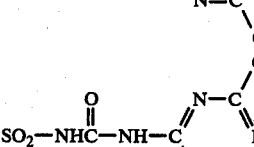 | 0.125 | &G,F,1C | 127 | 124 | 125 |
| | 0.5 | &G,F,2C | 120 | 113 | 79 |
| | 2.0 | &G,F,2C | 133 | 120 | 114 |

*F = delayed flowering

What is claimed is:

1. A compound having the formula:

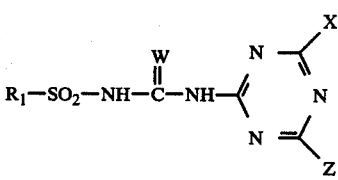

wherein
R₁ is

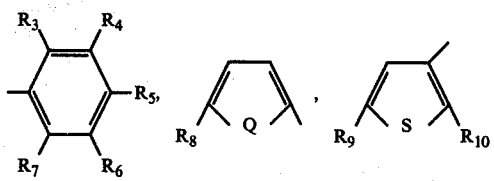 , 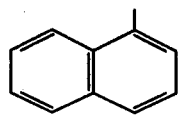 , 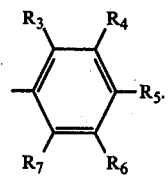 , $R_3$ and $R_6$ are independently hydrogen, fluorine, chlorine, bromine, iodine, alkyl of 1–4 carbon atoms, alkoxy of 1–4 carbon atoms, nitro, trifluoromethyl, cyano, $CH_3S(O)_n-$ or $CH_3CH_2S(O)_n-$;

$R_4$ is hydrogen, fluorine, bromine or methyl;

$R_5$ is hydrogen, fluorine, chlorine, bromine, methyl or methoxy;

$R_7$ is hydrogen, fluorine, chlorine, bromine, alkyl of 1–2 carbon atoms or alkoxy of 1–2 carbon atoms;

$R_8$ is hydrogen, methyl, chlorine or bromine;

$R_9$ and $R_{10}$ are independently hydrogen, methyl, chlorine or bromine;

W and Q are independently oxygen or sulfur;

$n$ is 0, 1 or 2;

X is hydrogen, chlorine, bromine, methyl, ethyl, alkoxy of 1–3 carbon atoms, trifluoromethyl, $CH_3S-$ or $CH_3OCH_2-$; and Z is methyl or methoxy; or an agriculturally suitable salt thereof;

provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

2. A compound of claim 1 wherein
$R_1$ is

3. A compound of claim 2 wherein $R_3$ is hydrogen, fluorine, chlorine, bromine, alkyl of 1–4 carbon atoms, alkoxy of 1–4 carbon atoms, nitro, $CH_3S-$ or $CH_3CH_2S-$; and $R_5$ is hydrogen, fluorine, chlorine, bromine or methyl; and $R_6$ is hydrogen, fluorine, chlorine, bromine, alkyl of 1–4 carbon atoms, alkoxy of 1–4 carbon atoms, trifluoromethyl, nitro, $CH_3S-$ or $CH_3CH_2S-$;

provided that:

(a) when $R_5$ is other than hydrogen $R_3$, $R_6$ or $R_7$ must independently be hydrogen, fluorine, chlorine, bromine, methyl or methoxy, and $R_4$ must be hydrogen, fluorine, chlorine, bromine or methyl.

4. A compound of claim 3 wherein
X is methyl or alkoxy of 1-3 carbon atoms; and Z is methoxy.

5. A compound of claim 4 wherein
$R_3$ is hydrogen, fluorine, chlorine, bromine, alkyl of 1-2 carbon atoms, alkoxy of 1-2 carbon atoms, nitro, $CH_3S$— or $CH_3CH_2S$—; and
$R_4$, $R_5$ and $R_7$ are independently hydrogen, fluorine, chlorine or methyl; and
$R_6$ is hydrogen, fluorine, chlorine, bromine, alkyl of 1-2 carbon atoms, alkoxy of 1-2 carbon atoms, trifluoromethyl, nitro, $CH_3S$—, or $CH_3CH_2S$—.

6. A compound of claim 5 wherein $R_3$ is nitro and each of $R_4$, $R_5$, $R_6$ and $R_7$ is hydrogen.

7. A compound of claim 4 wherein
$R_3$, $R_4$, $R_5$, $R_6$ and $R_7$ are independently hydrogen, fluorine, chlorine or methyl.

8. A compound of claim 4 wherein
$R_3$ is fluorine, chlorine or methyl; and
$R_4$, $R_5$, $R_6$ and $R_7$ are independently hydrogen, fluorine, chlorine or methyl;
provided that:
when $R_5$ is other than hydrogen, $R_4$ and $R_6$ must be hydrogen.

9. A compound of claim 4 wherein
$R_3$ is fluorine, chlorine or methyl; and
$R_4$ and $R_6$ are hydrogen; and
$R_5$ and $R_7$ are independently hydrogen, fluorine, chlorine or methyl.

10. A compound of claim 4 wherein
$R_3$ is hydrogen, fluorine, chlorine, bromine, alkyl of 1-4 carbon atoms, alkoxy of 1-4 carbon atoms, $CH_3S$—, or $CH_3CH_2S$—; and
$R_4$, $R_5$ and $R_7$ are hydrogen; and
$R_6$ is hydrogen, fluorine, chlorine, bromine, alkyl of 1-4 carbon atoms, alkoxy of 1-4 carbon atoms, trifluoromethyl, nitro, $CH_3S$— or $CH_3CH_2S$.

11. A compound of claim 10 wherein
$R_3$ is fluorine, chlorine, bromine, alkyl of 1-2 carbon atoms or alkoxy of 1-2 carbon atoms; and
$R_6$ is hydrogen, fluorine, chlorine, bromine, alkyl of 1-2 carbon atoms, alkoxy of 1-2 carbon atoms, trifluoromethyl or nitro.

12. A compound of claim 10 wherein
$R_3$ is fluorine, chlorine, bromine, methyl or methoxy; and
$R_6$ is hydrogen, fluorine, chlorine, bromine, methyl, methoxy or nitro.

13. A compound of claim 1 wherein
$R_1$ is

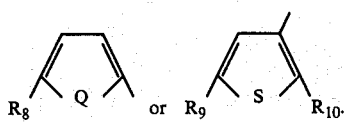

14. A compound of claim 13 wherein
Q is sulfur;
X is methyl or alkoxy of 1-3 carbon atoms; and
Z is methoxy.

15. A compound of claim 13 wherein
$R_1$ is

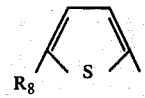

and $R_8$ is hydrogen.

16. A compound of claim 1 wherein
$R_1$ is

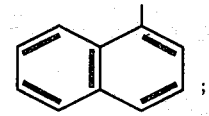

and W is oxygen.

17. A compound of claim 1 which is N-[(4-methoxy-6-methyl-1,3,5-triazin-2-yl)aminocarbonyl]-2-chlorobenzenesulfonamide.

18. A compound of claim 1 which is N-[(4,6-dimethoxy-1,3,5-triazin-2-yl)aminocarbonyl]-2-chlorobenzenesulfonamide.

19. A compound of claim 1 which is N-[(4,6-dimethoxy-1,3,5-triazin-2-yl)aminocarbonyl]-2,5-dimethoxybenzenesulfonamide.

20. A compound of claim 1 which is N-[(4,6-dimethoxy-1,3,5-triazin-2-yl)aminocarbonyl]-benzenesulfonamide.

21. A compound of claim 1 which is N-[(4-methoxy-6-methyl-1,3,5-triazin-2-yl)aminocarbonyl]-2-chloro-5-methoxybenzenesulfonamide.

22. A compound of claim 1 which is N-[(4-methoxy-6-methyl-1,3,5-triazin-2-yl)aminocarbonyl]-benzenesulfonamide.

23. A compound of claim 1 which is N-[(4,6-dimethyl-1,3,5-triazin-2-yl)aminocarbonyl]-benzensulfonamide.

24. A compound of claim 1 which is N-[(4,6-dimethoxy-1,3,5-triazin-2-yl)aminocarbonyl]-2-nitrobenzenesulfonamide.

25. A compound of claim 1 which is N-[(4-methoxy-6-methyl-1,3,5-triazin-2-yl)aminocarbonyl]-2-nitrobenzenesulfonamide.

26. A compound of claim 1 which is N-[(4-methoxy-6-methyl-1,3,5-triazin-2-yl)aminocarbonyl]-2,6-dichlorobenzenesulfonamide.

27. A composition suitable for controlling the growth of undesired vegetation which comprises an effective amount of a compound of claim 1 and at least one of the following: surfactant, solid or liquid diluent.

28. A composition suitable for controlling the growth of undesired vegetation which comprises an effective amount of a compound of claim 2 and at least one of the following: surfactant, solid or liquid diluent.

29. A composition suitable for controlling the growth of undesired vegetation which comprises an effective amount of a compound of claim 3 and at least one of the following: surfactant, solid or liquid diluent.

30. A composition suitable for controlling the growth of undesired vegetation which comprises an effective amount of a compound of claim 4 and at least one of the following: surfactant, solid or liquid diluent.

31. A composition suitable for controlling the growth of undesired vegetation which comprises an effective amount of a compound of claim 5 and at least one of the following: surfactant, solid or liquid diluent.

32. A composition suitable for controlling the growth of undesired vegetation which comprises an effective amount of a compound of claim 6 and at least one of the following: surfactant, solid or liquid diluent.

33. A composition suitable for controlling the growth of undesired vegetation which comprises an effective amount of a compound of claim 7 and at least one of the following: surfactant, solid or liquid diluent.

34. A composition suitable for controlling the growth of undesired vegetation which comprises an effective amount of a compound of claim 8 and at least one of the following: surfactant, solid or liquid diluent.

35. A composition suitable for controlling the growth of undesired vegetation which comprises an effective amount of a compound of claim 9 and at least one of the following: surfactant, solid or liquid diluent.

36. A composition suitable for controlling the growth of undesired vegetation which comprises an effective amount of a compound of claim 10 and at least one of the following: surfactant, solid or liquid diluent.

37. A composition suitable for controlling the growth of undesired vegetation which comprises an effective amount of a compound of claim 11 and at least one of the following: surfactant, solid or liquid diluent.

38. A composition suitable for controlling the growth of undesired vegetation which comprises an effective amount of a compound of claim 12 and at least one of the following: surfactant, solid or liquid diluent.

39. A composition suitable for controlling the growth of undesired vegetation which comprises an effective amount of a compound of claim 13 and at least one of the following: surfactant, solid or liquid diluent.

40. A composition suitable for controlling the growth of undesired vegetation which comprises an effective amount of a compound of claim 14 and at least one of the following: surfactant, solid or liquid diluent.

41. A composition suitable for controlling the growth of undesired vegetation which comprises an effective amount of a compound of claim 15 and at least one of the following: surfactant, solid or liquid diluent.

42. A composition suitable for controlling the growth of undesired vegetation which comprises an effective amount of a compound of claim 16 and at least one of the following: surfactant, solid or liquid diluent.

43. A composition suitable for controlling the growth of undesired vegetation which comprises an effective amount of the compound of claim 17 and at least one of the following: surfactant, solid or liquid diluent.

44. A composition suitable for controlling the growth of undesired vegetation which comprises an effective amount of the compound of claim 18 and at least one of the following: surfactant, solid or liquid diluent.

45. A composition suitable for controlling the growth of undesired vegetation which comprises an effective amount of the compound of claim 19 and at least one of the following: surfactant, solid or liquid diluent.

46. A composition suitable for controlling the growth of undesired vegetation which comprises an effective amount of the compound of claim 20 and at least one of the following: surfactant, solid or liquid diluent.

47. A composition suitable for controlling the growth of undesired vegetation which comprises an effective amount of the compound of claim 21 and at least one of the following: surfactant, solid or liquid diluent.

48. A composition suitable for controlling the growth of undesired vegetation which comprises an effective amount of the compound of claim 22 and at least one of the following: surfactant, solid or liquid diluent.

49. A composition suitable for controlling the growth of undesired vegetation which comprises an effective amount of the compound of claim 23 and at least one of the following: surfactant, solid or liquid diluent.

50. A composition suitable for controlling the growth of undesired vegetation which comprises an effective amount of the compound of claim 24 and at least one of the following: surfactant, solid or liquid diluent.

51. A composition suitable for controlling the growth of undesired vegetation which comprises an effective amount of the compound of claim 25 and at least one of the following: surfactant, solid or liquid diluent.

52. A composition suitable for controlling the growth of undesired vegetation which comprises an effective amount of the compound of claim 26 and at least one of the following: surfactant, solid or liquid diluent.

53. A composition suitable for use as a growth regulant which comprises an effective amount of a compound of claim 1 and at least one of the following: surfactant, solid or liquid diluent.

54. A composition suitable for use as a growth regulant which comprises an effective amount of a compound of claim 9 and at least one of the following: surfactant, solid or liquid diluent.

55. A composition suitable for use as a growth regulant which comprises an effective amount of the compound of claim 17 and at least one of the following: surfactant, solid or liquid diluent.

56. A composition suitable for use as a growth regulant which comprises an effective amount of the compound of claim 20 and at least one of the following: surfactant, solid or liquid diluent.

57. A composition suitable for use as a growth regulant which comprises an effective amount of the compound of claim 22 and at least one of the following: surfactant, solid or liquid diluent.

58. A composition suitable for use as a growth regulant which comprises an effective amount of the compound of claim 23 and at least one of the following: surfactant, solid or liquid diluent.

59. A method for controlling the growth of undesired vegetation which comprises applying to the locus to be protected an effective amount of a compound of claim 1.

60. A method for controlling the growth of undesired vegetation which comprises applying to the locus to be protected an effective amount of a compound of claim 2.

61. A method for controlling the growth of undesired vegetation which comprises applying to the locus to be protected an effective amount of a compound of claim 3.

62. A method for controlling the growth of undesired vegetation which comprises applying to the locus to be protected an effective amount of a compound of claim 4.

63. A method for controlling the growth of undesired vegetation which comprises applying to the locus to be protected an effective amount of a compound of claim 5.

64. A method for controlling the growth of undesired vegetation which comprises applying to the locus to be protected an effective amount of a compound of claim 6.

65. A method for controlling the growth of undesired vegetation which comprises applying to the locus to be protected an effective amount of a compound of claim 7.

66. A method for controlling the growth of undesired vegetation which comprises applying to the locus to be protected an effective amount of a compound of claim 8.

67. A method for controlling the growth of undesired vegetation which comprises applying to the locus to be protected an effective amount of a compound of claim 9.

68. A method for controlling the growth of undesired vegetation which comprises applying the the locus to be protected an effective amount of a compound of claim 10.

69. A method for controlling the growth of undesired vegetation which comprises applying to the locus to be protected an effective amount of a compound of claim 11.

70. A method for controlling the growth of undesired vegetation which comprises applying to the locus to be protected an effective amount of a compound of claim 12.

71. A method for controlling the growth of undesired vegetation which comprises applying to the locus to be protected an effective amount of a compound of claim 13.

72. A method for controlling the growth of undesired vegetation which comprises applying to the locus to be protected an effective amount of a compound of claim 14.

73. A method for controlling the growth of undesired vegetation which comprises applying to the locus to be protected an effective amount of a compound of claim 15.

74. A method for controlling the growth of undesired vegetation which comprises applying to the locus to be protected an effective amount of a compound of claim 16.

75. A method for controlling the growth of undesired vegetation which comprises applying to the locus to be protected an effective amount of the compound of claim 17.

76. A method for controlling the growth of undesired vegetation which comprises applying to the locus to be protected an effective amount of the compound of claim 18.

77. A method for controlling the growth of undesired vegetation which comprises applying to the locus to be protected an effective amount of the compound of claim 19.

78. A method for controlling the growth of undesired vegetation which comprises applying to the locus to be protected an effective amount of the compound of claim 20.

79. A method for controlling the growth of undesired vegetation which comprises applying to the locus to be protected an effective amount of the compound of claim 21.

80. A method for controlling the growth of undesired vegetation which comprises applying to the locus to be protected an effective amount of the compound of claim 22.

81. A method for controlling the growth of undesired vegetation which comprises applying to the locus to be protected an effective amount of the compound of claim 23.

82. A method for controlling the growth of undesired vegetation which comprises applying to the locus to be protected an effective amount of the compound of claim 24.

83. A method for controlling the growth of undesired vegetation which comprises applying to the locus to be protected an effective amount of the compound of claim 25.

84. A method for controlling the growth of undesired vegetation which comprises applying to the locus to be protected an effective amount of the compound of claim 26.

85. A method for selectively controlling the growth of undesired vegetation in wheat comprising applying to the locus of such undesired vegetation an effective amount of a compound of claim 1.

86. A method for selectively controlling the growth of undesired vegetation in wheat comprising applying to the locus of such undesired vegetation an effective amount of a compound of claim 2.

87. A method for selectively controlling the growth of undesired vegetation in wheat comprising applying to the locus of such undesired vegetation an effective amount of a compound of claim 3.

88. A method for selectively controlling the growth of undesired vegetation in wheat comprising applying to the locus of such undesired vegetation an effective amount of a compound of claim 4.

89. A method for selectively controlling the growth of undesired vegetation in wheat comprising applying to the locus of such undesired vegetation an effective amount of a compound of claim 5.

90. A method for selectively controlling the growth of undesired vegetation in wheat, comprising applying to the locus of such undesired vegetation an effective amount of a compound of claim 6.

91. A method for selectively controlling the growth of undesired vegetation in wheat, comprising applying to the locus of such undesired vegetation an effective amount of a compound of claim 7.

92. A method for selectively controlling the growth of undesired vegetation in wheat, comprising applying to the locus of such undesired vegetation an effective amount of a compound of claim 8.

93. A method for selectively controlling the growth of undesired vegetation in wheat, comprising applying to the locus of such undesired vegetation an effective amount of a compound of claim 9.

94. A method for selectively controlling the growth of undesired vegetation in wheat, comprising applying to the locus of such undesired vegetation an effective amount of a compound of claim 10.

95. A method for selectively controlling the growth of undesired vegetation in wheat, comprising applying to the locus of such undesired vegetation an effective amount of a compound of claim 11.

96. A method for selectively controlling the growth of undesired vegetation in wheat, comprising applying to the locus of such undesired vegetation an effective amount of a compound of claim 12.

97. A method for selectively controlling the growth of undesired vegetation in wheat, comprising applying to the locus of such undesired vegetation an effective amount of a compound of claim 13.

98. A method for selectively controlling the growth of undesired vegetation in wheat, comprising applying to the locus of such undesired vegetation an effective amount of a compound of claim 14.

99. A method for selectively controlling the growth of undesired vegetation in wheat, comprising applying to the locus of such undesired vegetation an effective amount of a compound of claim 15.

100. A method for selectively controlling the growth of undesired vegetation in wheat which comprises applying to the locus of the undesired vegetation an effective amount of a compound of claim 16.

101. A method for selectively controlling the growth of undesired vegetation in wheat which comprises applying to the locus of the undesired vegetation an effective amount of the compound of claim 17.

102. A method for selectively controlling the growth of undesired vegetation in wheat which comprises applying to the locus of the undesired vegetation an effective amount of the compound of claim 18.

103. A method for selectively controlling the growth of undesired vegetation in wheat which comprises applying to the locus of the undesired vegetation an effective amount of the compound of claim 19.

104. A method for controlling the growth of water hyacinth which comprises applying thereto an effective amount of a compound of claim 1.

105. A method for controlling the growth of water hyacinth which comprises applying thereto an effective amount of a compound of claim 10.

106. A method for controlling the growth of water hyacinth which comprises applying thereto an effective amount of the compound of claim 17.

107. A method for controlling the growth of water hyacinth which comprises applying thereto an effective amount of the compound of claim 20.

108. A method for controlling the growth of water hyacinth which comprises applying thereto an effective amount of the compound of claim 21.

109. A method for regulating the growth of vegetation which comprises applying to the locus of the vegetation an effective amount of a compound of claim 1.

110. A method for regulating the growth of vegetation which comprises applying to the locus of the vegetation an effective amount of a compound of claim 10.

111. A method for regulating the growth of vegetation which comprises applying to the locus of the vegetation an effective amount of the compound of claim 17.

112. A method for regulating the growth of vegetation which comprises applying to the locus of the vegetation an effective amount of the compound of claim 20.

113. A method for regulating the growth of vegetation which comprises applying to the locus of the vegetation an effective amount of the compound of claim 22.

114. A method for regulating the growth of vegetation which comprises applying to the locus of the vegetation an effective amount of the compound of claim 23.

* * * * *